US005436395A

United States Patent [19]
Sondahl et al.

[11] Patent Number: 5,436,395
[45] Date of Patent: Jul. 25, 1995

[54] INDUCTION AND SELECTION OF SOMACLONAL VARIATION IN COFFEE

[75] Inventors: Maro R. Sondahl, Cherry Hill; William R. Romig, Moorestown; Alvina Bragin, Cherry Hill, all of N.J.

[73] Assignee: Kraft Foods, Inc., Northfield, Ill.

[21] Appl. No.: 269,964

[22] Filed: Jun. 30, 1994

Related U.S. Application Data

[63] Continuation of Ser. No. 997,417, Dec. 28, 1992, abandoned, which is a continuation-in-part of Ser. No. 617,453, Nov. 23, 1990, which is a continuation of Ser. No. 268,326, Nov. 7, 1988, abandoned.

[51] Int. Cl.$^6$ ............................................. A01H 5/00
[52] U.S. Cl. ............................. 800/230; 800/DIG. 9
[58] Field of Search ......... 800/205, 200, 230, DIG. 9; 47/58.03; 435/240.4, 45.49

[56] References Cited

U.S. PATENT DOCUMENTS 4,616,100  10/1986  McHughen .................... 800/200
5,107,065   4/1992  Shewmaker .................... 800/205

OTHER PUBLICATIONS

Carvalho et al. (1990) Biological Abstracts #89:37867.
Carvalho et al. (1991) Biological Abstracts #92:28915.
Keller et al. (1972) "Caffeine Synthesis in Fruits and Tissue Cultures of *Coffea arabica*", *Planta.* 108, 339–350.
Townsley (1974) "Production of Coffee from Plant Cell Suspension Cultures", *Can. Inst. Food Sci. Technol. J.* 7, 79–81.
Buckland et al. (1975) "Coffee Cell Suspension Cultures Caffeine and Chlorogenic Acid Content", *J. Inst. Can. Sci. Technol. Aliment* 8, 164–165.
van de Voort et al. (1975) "Comparison of the Unsaponifiable Lipids Isolated from Coffee Cell Cultures and from Green Coffee Beans", *J. Inst. Can. Sci. Technol. Aliment* 8, 199–201.
Sondahl et al. (1977) "High Frequency Induction of Somatic Embryos in Cultured Leaf Explants of *Coffea arabica L.*", *Z. Pflanzenphysiol Bd.* 81, 395–408.
Frischknecht et al. (1977) "Tissue Culture of *Coffea arabica* Growth and Caffeine Formation", *Plant Medica* 31, 344–350.
Sondahl et al. (1979) "Histological Study of High Frequency and Low Frequency Induction of Somatic Embryos in Cultured Leaf Explants of *Coffea arabica L.*", *Z. Pflanzenphysiol Bd.* 81, 395–408.
Hanna et al. (1984) "Uniformity of Plants Regenerated from Somatic Embryos of *Panicum maximum* Jacq", *Theoret. Appl. Genet.* 67, 155–159.
Sondahl et al. (1984) "Coffee", in *Handbook of Plant Cell Culture* 3, Ammrato et al., eds., Macmillan Press.
Baumann (1985) "Biotechnology, Its Potential for the Growth and Manufacture of Coffee", Association Scientifique Internationale du Cafe, Colloque, pp. 55–68, Lome.
Yasuda et al. (1986) "Somatic Embryogenesis from Coffee Callus and Protoplast", *Abstr. Int. Congr. Plant Tiss. Cell Cult.*, 137.

(List continued on next page.)

*Primary Examiner*—Gary Benzion
*Attorney, Agent, or Firm*—Thomas A. Marcoux; Thomas R. Savoie

[57] ABSTRACT

This invention relates to somaclonal variants from different varieties of coffee plants. The invention also contemplates methods for the high frequency generation of and the low frequency generation of said somaclonal variants in coffee plants, thereby providing variants with improved processing and agronomic characteristics. Among these somaclonal variants are high-yielding, low caffeine *Coffea arabica* cv. *Laurina* somaclones and a method for producing same. In particular, this invention relates to the unique application of tissue culture methodology as new methods for variety development, breeding and then the scale-up of the selected superior genotypes of coffee plants for the commercial production of coffee.

5 Claims, 1 Drawing Sheet

OTHER PUBLICATIONS

Menendez et al. (1987) "Somatic Embryogenesis from Leaf Explants of Catimor Coffee", *Cafe Cacao The* 31, 15–22.

Scowcroft (1985) "Somaclonal Variation: The Myth of Clonal Uniformity", in *Plant Gene Research* Ed. Holin and Dennis, Springer Verlag, 220.

Larkin et al. (1981) "Somaclonal Variation—A Novel Source of Variability from Cell Cultures for Plant Improvement", *Theor. Appl. Genet.* 60, 197–214.

Swedlund et al. (1985) "Cytogenetic Characterization of Embryogenic Callus and Regenerated Plants of *Pennisetum Americanum* (L.) K. Schum", *Theor. Appl. Genet.* 69, 575–581.

Baumann et al. (1988) "Caffeine: Production by Plant (coffea spp.) Cell Cultures" in: *Biotechnology in Agriculture and Forestry, vol. 4, Medicinal and Aromatic Plants I*, Bajaj, Ed., Springer Verlag, Berlin, pp. 264–281.

George et al. (1984) *Plant Propagation by Tissue Culture*, Exegetics Ltd., Eversley, Great Britain, pp. 470–471.

Monaco et al. (1977) "Applications of Tissue Culture in the Improvement of Coffee" in: *Applied and Fundamental Aspects of Plant Cell, Tissue and Organ Culture*, Reinert et al., eds., Springer Verlag, Berlin, pp. 109–129.

Sondahl et al. (1979) "Research in Coffea spp. and Applications of Tissue Culture Methods" in: *Plant Cell and Tissue Culture: Principles and Applications*, Sharp et al., eds., MacMillan, New York, pp. 527–584.

Plant Breeding Abstracts, Coffee Biotechnology, No. 969583.

Plant Breeding Abstracts, Coffee, No. 1405101.

INDUCTION AND SELECTION OF SOMACLONAL VARIATION IN COFFEE

This is a continuation of application Ser. No. 997,417, filed on Dec. 28 1992, now abandoned, which is a C-I-P of Ser. No. 617,453, filed Nov. 23, 1990, which is a continuation of Ser. No. 268,326, filed Nov. 7, 1988, now abandoned.

FIELD OF INVENTION

This invention relates to somaclonal variants from different varieties of coffee plants. The invention also contemplates a method for the high frequency generation of said somaclonal variants in coffee plants, thereby providing variants with improved processing and agronomic characteristics. In particular, this invention relates to the unique application of tissue culture methodology as new methods for variety development, breeding and then the scale-up of the selected superior genotypes of coffee plants for the commercial production of coffee, including high yielding Laurina somaclones.

BACKGROUND OF THE INVENTION

There are two commercial coffee species, *Coffea arabica* L. (arabica type coffee) and *Coffea canephora* p. ex Fr. (*canephora* or Robusta type coffee). Coffee is a tropical and perennial tree which produces coffee berries. The coffee beverage is produced by percolating hot water through roasted coffee seeds. Arabica coffee provides a superior coffee beverage and it is typical of the highland growing regions while Robusta coffee produces a lower quality coffee and is grown in lowland regions.

A breeding cycle for coffee plants takes four years, i.e., seeds to a flowering plant and back to seeds. Selections for yield are usually made from 6–8 year old coffee plants. Several cycles of crossings and selections are required until one finds superior genotypes. In order to assure fidelity through seed propagation, six cycles of selfing are required. Considering one cycle for hybridization and selection and six cycles for seed homozygosity, a normal coffee breeding program requires 28 years. Cell culture techniques, such as somatic embryogenesis, clonal propagation, and protoplast regeneration provide opportunities to shorten the time requirement for coffee improvement.

The pioneer cell culture work on coffee was reported by Staritsky, Acta Bot. Neerl. 19:509–514, 1970, who described the induction of somatic embryos and plantlets from orthotropic shoots of *C. canephora*. Subsequently, Colona, Cafe Cacao The 6:193–203, 1972, established cultures of embryos of *C. canephora* and *Coffea dewevrei*. Pursuant to the study of caffeine synthesis, Keller et al. Planta 108:339–350, 1972, induced callus from endosperm tissues of *C. arabica*. Sharp et al. Phyton 31:67–74, 1973, cultured somatic and haploid tissues of *C. arabica*, obtaining callus growth (petioles, leaves, green fruit), proembryo formation (anthers) and shoot development (orthotropic shoots). Induction of abundant friable callus from perisperm tissues of *C. arabica* and *Coffea stenophylla* was reported by Monaco et al. Applied and Fundamental Aspects of Plant Cell, Tissue, and Organ Culture, J. Reinert and Y. P. S. Bajaj, eds., pp 109–129, 1977 Springer-Verlag, Berlin. Furthermore, perisperm proliferated rapidly in the absence of auxin, suggesting that it was autonomous for auxin. Liquid cell cultures of *C. arabica* cv. *El Salvador* derived from orthotropic shoots were reported by Townsley, Can. Inst. Food Sci. Technol. J. 7:79–81, 1974. These same suspension cultures were used to analyze caffeine and chlorogenic acid contents by Buckland and Townsley, J. Inst. Can. Sci. Technol. Aliment 8:164–165, 1975, and to compare unsaponifiable lipids in green beans with those in cell suspensions as reported by van der Voort and Townsley, J. Inst. Can. Sci. Technol. Aliment 8:199–201, 1975. Subsequently, Sondahl and Sharp, Z. Pflanzenphysiol. 81:395–408, 1977; Plant Cell and Tissue Culture: Principles and Applications, W. R. Sharp, P. O. Larsen, E. F. Paddock and V. Raghavan, eds., pp 527–584, 1979, Ohio State Univ. Press, Columbus, distinguished between high and low frequencies of somatic embryo induction from cultured mature leaf explants of *C. arabica* cv. *Bourbon*. A histological study demonstrated the somatic embryos from coffee leaf explants were derived from mesophyll cells. Furthermore, low frequency somatic embryos (LFSE) were present as early as 70 days whereas embryogenic tissue and high frequency somatic embryos (HFSE) were detected only 90–120 days of secondary culture (Sondahl et al. Z. Pflanzenphysiol. 94:101–108, 1979). HFSEs were derived from a distinct cellular phenotype (small and round-shaped, ca. 20 mm diameter) in contrast with callus cells (long rods, ca. 150 mm long). Mature leaf cultures were capable of yielding HFSE.

In summary, plant regeneration from coffee tissue has been accomplished from solid cultures of orthotropic shoots and mature leaves covering four species of the Coffea and five *C. arabica* cultivars. More particularly, direct (LFSE) and indirect (HFSE) somatic embryogenesis routes are frequently associated with coffee tissues together with shoot development.

Cloning of selected coffee plants can be accomplished through nodal cultures or by development of embryogenic cell lines in liquid phase using bioreactor techniques. Characteristically, coffee plants have ten arrested orthotropic buds and two plagiotropic buds at each node of a coffee stem. The plagiotropic buds differentiate only after the 10th–11th node of a developing seedling, whereas the orthotropic buds are present beginning with the first node (cotyledonary node). The excision and culture of the uppermost nodes permits the recovery of cloned coffee plants from each orthotropic bud. These plants are clones of the donor plant. The technique to culture these nodal tissues and recover normal coffee plants from these axillary buds permits the application of this methodology for vegetative propagation of coffee plants. The advantage of bioreactor cloning is the utilization of embryogenic cells in a liquid medium and the recovery of a very large number of plants within a short period of time. For example, a one liter bioreactor could yield ca. 250,000 plantlets.

Somaclonal variation refers to the genetic variability found among plants derived from in vitro cultures of somatic cells. Variation in cultivated plant cells has been observed since the beginning of plant tissue culture. This variability was associated with chromosomal abnormalities due to long-term cell culture. Later, the recovery of plants with chromosome variation was reported in sugar cane and potato. It was then proposed as a novel source of agriculturally useful variation for crops. More recently, evidence has been presented that variant characters expressed in plants derived from the culture of somatic tissues are transmitted to the progeny. These results open the door for the use of cell culture as a tool to recover stable variation in any plant species.

Presently, somaclonal variation has been described in at least 16 plant species: tomato, potato, tobacco, rapeseed, celery, lettuce, garlic, pineapple, sugar cane, wheat, rice, corn, oat, barley, flax and sorghum. In the case of tomato, such variability has been genetically analyzed during the $R_0$, $R_1$ and $R_2$ generations. Chromosomal changes, as well as nuclear and cytoplasmic mutations, have been described. The origin of somaclonal variation can be explained by (a) chromosomal changes (rearrangements, deletions, number); (b) nuclear mutations; (c) organelle mutations; (d) mitotic crossing-over; and (e) cell sorting. Genetic analysis of nuclear mutations of somaclones have demonstrated several characteristics to be monogenic.

The events leading to somaclonal variation can take place during the ontogeny of the tissue (preexisting variation) or during the cell culture period (in vitro variation). The morphogenetic process of plant regeneration (organogenesis vs. embryogenesis), explant sources, genotypes and culture conditions are all important factors in determining the frequency of somaclonal variation.

Practical advantages of using somaclonal variation techniques for plant breeding resides in the fact that the variability may be associated with single gene mutations of somatic cells of commercial cultivars. As a consequence of this characteristic, the new variants are almost identical to the mother plant except for the new trait. Following two cycles of field testing to insure the stability of the new trait and yield performance of the selected somaclone lines, new plant varieties can be released within a shorter time than required by conventional breeding. This fact can be advantageous to plant breeders since it avoids the long cycles of selfings and backcrossings in order to eliminate the undesirable genes introduced during the original cross with the wild type. Another advantage to plant breeding is the access to new nuclear mutations and also to organelle mutations (genes coded in the cytoplasm) within a commercial genotype.

In a crop improvement program somaclonal variation methodology has to interface with conventional breeding. One obvious strategy is to introduce the best available varieties into cell culture and select for improved traits. Somaclonal variation can be used to uncover single gene mutations that retain all the favorable qualities of an existing variety. Several in vitro cycles can be used to further improve one particular genotype, (i.e., second, third, etc. generation of somaclones).

*Coffea arabica* cultivars were derived from a very narrow genetic reservoir. Although hybridization has been the primary method of developing new breeding lines, induced mutations could offer an opportunity to increase the range of genetic variability for the breeder. However, the data currently available indicate that cuttings, germinating seeds, and pollen grains of *C. arabica* are quite resistant to ionizing radiation such as gamma and x-rays (2–100 krad) and to chemical mutagens. Although a very large number of samples have been irradiated, no identifiable mutants have been isolated. Treatment of seeds with recognized powerful mutagens, e.g., EMS or sodium azide, have failed to produce a single distinct mutation despite examination of several thousands of plants. Somaclonal variation therefore, offers an excellent opportunity for developing unique types of genetic variability for the selection of new breeding lines of coffee plants. Furthermore, since somaclonal variants are derived from spontaneous mutations (nuclear or cytoplasmic), it will be possible to release new varieties in shorter periods of time provided that the cultures were derived from tissues of superior commercial coffee genotypes.

For example, Laurina is a natural mutant of *C. arabica* that retains the good Arabica taste but has only 50% of the Arabica caffeine content (0.7%), a highly desirable trait. Despite the fact that the Laurina mutation has been known since the late 1800's, Laurina plants have not been commercially viable due to low bean yields and susceptibility to diseases, particularly coffee leaf rust. Laurina arose as a natural mutation isolated from the Arabica coffee variety Bourbon and was first discovered at Reunion Island (21° latitude South), Africa. Laurina is also called "Bourbon Pointu" or "Ismirna coffee". The Laurina mutation has been characterized as a single recessive gene mutation (lr lr) with a pleiotropic effect on caffeine content (0.6–0.7%) and plant morphology (very small leaves, short internodes, short plant height, elongated fruits). Hence, Laurina has about a 50% reduction in caffeine content relative to Arabica varieties. Until the early 1990's, attempts were made to cultivate Laurina in small farms due to its good beverage quality, but were completely abandoned because of low yield. Consequently, Laurina somaclones which produce high an yield and have the naturally low caffeine content (or less) typical of the Laurina variety are highly desirable given the demand for decreasing the caffeine content of coffee products.

This invention, therefore, fulfills a long felt need to develop coffee variants with improved processing and agronomic characteristics and in particular, to develop methodologies to generate said variants in coffee species.

To date, somaclonal variants in coffee have not been reported. Genetic variation in coffee is considered rare due to its tetraploid nature. Additionally, appropriate tissue culture and field trial conditions have not been well established for coffee. Certain tissue culture conditions have been reported by Frischkneckt et al., Handbook of plant Cell Culture 3:564–590, 1984, Ammirate et al. Eds, Macmillan Press, New York, London. The use of biotechnology for coffee improvement is also discussed by Baumann, Association Scientifique Internationale du Cafe', Colloque, Lone', 55–68, 1985. Tissue culture conditions are also discussed by de Menendez, Cafe Cacao The 31:15–22, 1987.

SUMMARY OF THE INVENTION

Figure 1:
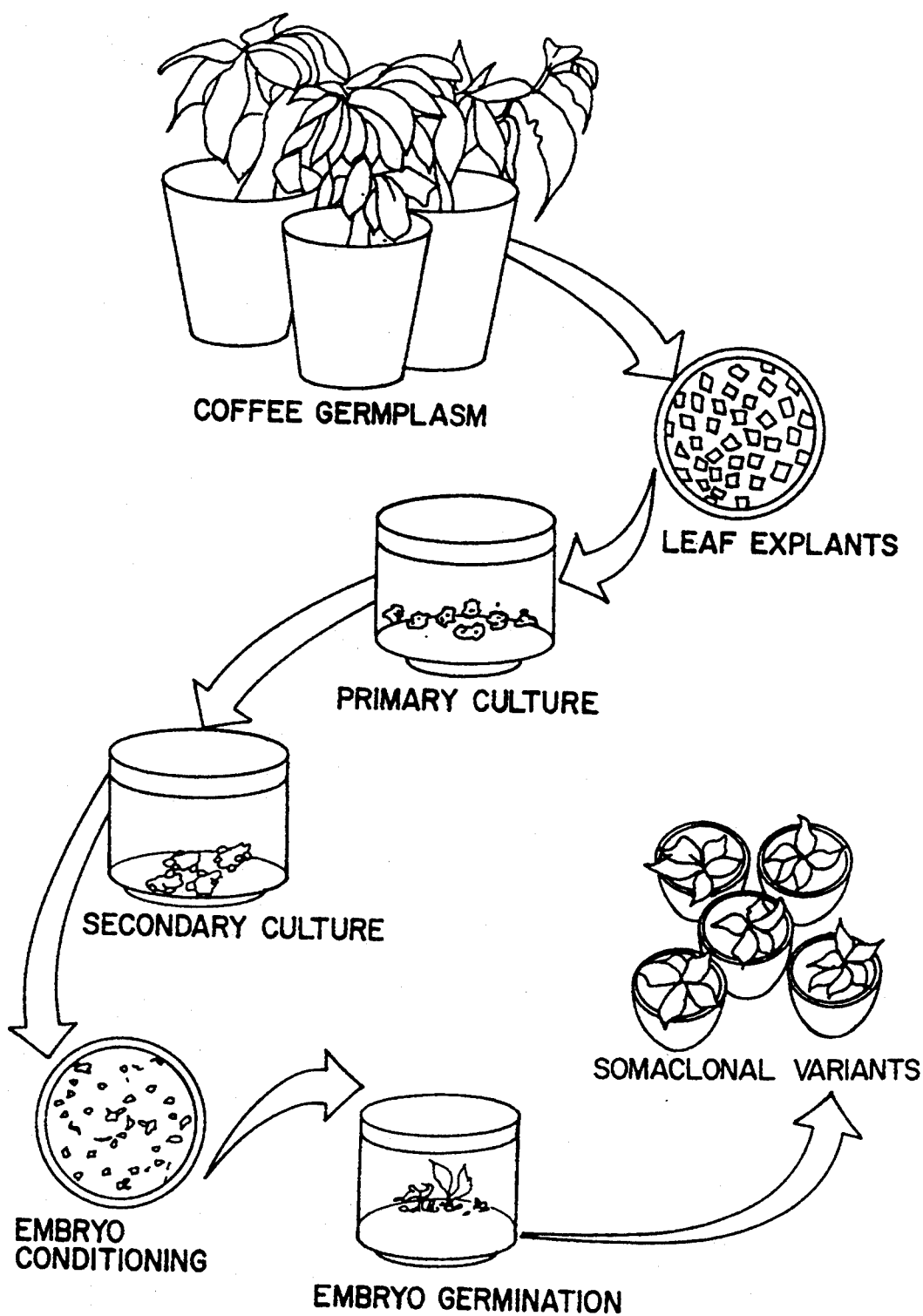
FIG. 1 is a pictorial representation of the production of somaclonal variants in coffee.

This invention relates to somaclonal variants from different varieties of coffee plants wherein said variants possess improved processing and agronomical characteristics.

This invention also contemplates a method of generating somaclonal variants from explants of the genus Coffea, comprising inducing the formation of coffee plants by somatic embryogenesis from somatic tissues and then screening said plants for off parental characteristics. In particular, one aspect of this invention relates to the formation of somatic embryos by the high frequency somatic embryogenic pathway (indirect embryogenesis). In another aspect of the invention, formation of somatic embryos is by the low frequency somatic embryogenic pathway (direct embryogenesis).

Still another aspect of the invention is the application of in vitro selection in combination with the method of generating somaclonal variants to express specific variants Yet another aspect of this invention provides a method for generating somaclonal variants of *C. arabica* cv. *Laurina* which are high-yielding but have a low caffeine content relative to other Arabica varieties. Laurina somaclones produced by this method are also provided.

DETAILED DESCRIPTION OF THE INVENTION

The present invention is directed to somaclonal variants in plants of the genus Coffea, wherein said variants exhibit improved processing and agronomical characteristics. This invention is predicated on the unique application of tissue culture methodologies to commercially growing coffee cultivars with the aim of rapid development of new coffee varieties. Somatic tissues, defined herein to include leaf, stem, petiole pieces and tissues such as flower petals, roots, mature and immature embryos and the like, are used in accordance with this invention to produce coffee somaclones, and selections are made for improved genetic traits found among this coffee somaclonal population.

In particular, this invention provides somaclonal variants of *C. arabica* cv. *Laurina* plants which exhibit increased cherry bean yields but maintain the naturally low caffeine content associated with the Laurina variety of coffee The generalized scheme for the production of somaclonal variants is shown in FIG. 1.

As used herein, polyploid refers to multiple copies of chromosome set. Variation means the traits contemplated herein.

In accordance with the subject invention, a method is disclosed for the generation of somaclonal variants from an explant of the genus Coffea comprising: (a) inducing formation of somatic embryos from said explant; (b) inducing formation of coffee plants by somatic embryogenesis from said embryos; and (c) screening said plants for off-parental characteristics. More particularly, Coffea explants are cultured under condition to induce formation of somatic embryos; the somatic embryos are cultured for a time and under conditions to induce formation of coffee plants by somatic embryogenesis; these plants are grown under nursery and/or field conditions; and somaclonal variants are recovered by screening the plants for off-parental characteristics.

Somaclonal variants can be prepared from any species in the genus Coffea including the species *C. arabica, C. canephora, C. dewevrei,* and *C. stenophylla* as well as *C. eugenioides, C. racemosa* and *C. liberica*. Preferably, variants are prepared from the commercial coffee species *C. arabica* L. (arabica type coffee) or *C. canephora* p. ex. Fr. (Robusta or canephora type coffee), and even more particularly from *C. arabica* cultivars which include *El Salvador, Mundo Novo, Icatu, Yellow Bourbon, Red Catuai, Yellow Catuai, Caturra, Catimor, Laurina, Aramosa* and *Typica*; as well as *Bourbon Amerelo, Bourbon Vermelho, Amarelo de Botucatu, Caturra Amarelo, Caturra Vermelho* and *Marogogipe AD.*

With respect to the induction of somatic embryo development, and in accordance with this invention, two method are contemplated: a high frequency somatic embryogenic pathway and a low frequency somatic embryogenic pathway. The high frequency or indirect pathway comprises: (a) contacting an explant from the genus Coffea with pre-incubation medium to form a primary culture; (b) transferring said primary culture to an induction medium to form callus; (c) transferring said callus to a conditioning medium for sufficient time to allow formation of embryogenic tissue; and (d) isolating the somatic embryos from said conditioning medium. The low frequency or direct pathway comprises: (a) contacting said explant with a pre-incubation medium to form a primary culture; (b) transferring said primary culture to a low frequency induction medium for sufficient the to allow formation of embryogenic tissue; and (c) isolating the somatic embryos from said low frequency induction medium.

In accordance with this invention, induction of somatic embryogenesis is accomplished by: (a) contacting somatic embryos with maturation medium to form coffee embryos; (b) transferring said coffee embryos to a germinating medium to form coffee plantlets; and (c) transferring said plantlets to soil for a time sufficient to allow for growth to plants.

In further accordance with this invention, the high frequency somatic embryogenic pathway, using the aforementioned plant regenerative techniques as applied to the genus Coffea, contemplates using any tissue as explant source but preferably the somatic tissues, leaf, stem and petiole pieces and tissues such as flower petals, roots, immature embryos and the like. In general, the plant tissue is surface sterilized with sodium hypochlorite at a concentration of from about 1% (w/v) to about 6% (w/v) for about 30 min. One skilled in the art will recognize the availability of other surface sterilizing agents, for example., detergents, bleaches, mecuric chloride, acids, bases and antimicrobial and antifungal agents; the artisan can also use physical sterilizing means, for example, radiation and certain gases. The plant tissue is excised to give an explant of from about 0.5 to about 20 mm$^2$ but in a preferred embodiment, explant of about 7 mm$^2$ is used. Excision of plant tissue is such that, with respect to leaf tissue, midvein and margins are avoided. Said explant is then subjected to a pre-incubation period on a saline-agar plate for from about 24 hours to about 60 hours but within a preferred range of 36 to 48 hours. The pre-incubation medium comprises half-strength MS inorganic salts containing thiamine (30 $\mu$M), cysteine (210 $\mu$M), inositol (550 $\mu$M), sucrose (87 mM) and agar (8 g/l).

The sterile, pre-incubated explants with normal coloration and viability are then transferred to an induction medium wherein the mixture is said to be a primary culture. The induction medium comprises basal medium defined herein to comprise MS inorganic salts, thiamine (30 $\mu$M), cysteine (210 $\mu$M), inositol (550 $\mu$M), sucrose (117 $\mu$M) and agar (8 g/l).

The induction medium also contains the growth regulators kinetin (KIN, 5-20 $\mu$M) and 2,4-dichlorophenoxyacetic acid (2,4-D, 0.5-5 $\mu$M). The artisan will immediately recognize other growth regulators such as $\alpha$-naphthyleneacetic acid (NAA), 6-benzylaminopurine (6-BA), indoleacetic acid (IAA), indole-3-butyric acid (IBA), (4-chlorophenoxy) acetic acid (CPA), picloram (4-amino-3,5,6-trichloropicolinic acid (PIC)), zeatin (ZEA), 2-naphthoxyacetic acid (NOA), (2-isopentenyl) adenine (2iP), 2-benzothiazoleacetic acid, 2,4,5-trichlorophenoxyacetic acid (2,4,5-T) or chemically equivalent analogs thereof. The primary culture is retained in the induction medium in the dark for from about 7 to about 8 weeks at from about 23° to about 28° C. although these parameters may vary depending on explant source.

The primary culture is then transferred to a "conditioning medium" wherein said culture is referred to as the secondary culture. The conditioning medium comprises basal medium with half-strength MS salts, except that $KNO_3$ is added to twice the concentration. Increased concentration of $KNO_3$ is not essential for success but improves results. To said conditioning medium is also added growth regulators KIN (0.5–3.0 $\mu$M) and NAA (0.1–2.0 $\mu$M) but other similarly acting regulators as listed above may also be substituted. The secondary culture is maintained under lights for from about 12 to about 16 weeks in which time the original callus develops a brown color. Within about 13 to 16 weeks after subculture to conditioning medium, the embryogenic tissue (white-cream color and friable) emerges from the periphery of the original callus mass. After about 3 to 6 more weeks, clusters of globular-shaped somatic embryos develop.

The somatic embryos developed in accordance with this invention and described above, are isolated and transferred to a maturation medium comprising half-strength MS inorganic salts, thiamine (3–30 $\mu$M), nicotinic acid (1–15 $\mu$M), pyridoxine (1–15 $\mu$M), inositol (50–550 $\mu$M), zeatin or 2-iP (0.1–5.0 $\mu$M), NAA (0.25 $\mu$M), abscisic acid (0.02–0.25 $\mu$M), or up to 20 $\mu$M abscisic acid, cysteine (50–200 mg/l), PVP (1–10 g/l), charcoal (2 g/l) sucrose (10–40 g/l) and agar (7 g/l). The pH of said medium is adjusted to about pH 5.5 before autoclaving and incubation is in dark or dim light for from about 4 to about 8 weeks. After this time, coffee embryos are transferred to a germination medium comprising half-strength MS salts, thiamine (3–30 $\mu$M), nicotinic acid (1–15 $\mu$M), pyridoxine (1–15 $\mu$M), inositol (50–550 $\mu$M), sucrose (20 g/l), zeatin or 2-iP (0.5–2.5 pM), abscisic acid (0.05 $\mu$M), cysteine (200 mg/l), PVP-40 (10 g/l), gelrite (2.4 g/l), at a pH before autoclaving of about pH 5.5. The culture are maintained in the incubator at from about 24° C. to about 28° C. at 16 hours photoperiod under a light intensity of from about 200 to about 1,000 foot candles. The somatic embryos are allowed to germinate, preferably inside a petri dish, a 4 ounce glass or jar, or individually inside 20×150 mm test tubes.

Following from about 4 to about 8 weeks on the germination medium, coffee plantlets are removed and transferred to plastic boxes (Magenta TM containers) filled with the following substrate: 1:1 unit of Metromix 200 TM and peat moss, half-strength MS inorganic salts and zeatin or 2-iP (0.5–2.0 $\mu$M). These containers are sterilized by autoclaving and five plantlets can be used per each vessel. Containers are incubated at from about 24° C. to about 20° C., for about 16 hours of light, with a light intensity of about 200 to about 1,000 foot candles for approximately 4 to 6 weeks. After this period, Magenta containers are transferred to a shaded portion of greenhouse (20% sunlight) for further plantlet development. Plants with 2 to 4 pairs of leaves are transferred to the same soil mix as above and kept under a fog condition for about 2 to about 4 weeks. Each coffee plant is raised inside a 10 cubic inch growing cone. After this adaptation period, plants are removed to regular greenhouse conditions. Plants which are about 3 to 10 inches tall are shipped to a coffee nursery. After a period of about 4 to 8 months adaptation, coffee plants are transplanted to field conditions under a spacing of 2×3.5 m.

Plant regeneration by the low frequency somatic embryogenic pathway is also contemplated in accordance with the present invention. The explant is obtained, sterilized and preincubated according to the aforementioned high frequency M somatic embryogenic pathway. The viable explant is then transferred to a low frequency induction medium comprising full-strength MS inorganic salts, thiamine (3–30 $\mu$M), nicotinic acid (1–15 $\mu$M), pyridoxin (1–15 $\mu$M), cysteine (50–200 $\mu$M), sucrose (30 g/l), inositol (50–500 $\mu$M), zeatin or 2-iP (5–15 $\mu$M), 2,4-D (0.5–1.0 $\mu$M) and agar (7 g/l), in said medium having a pH before sterilization by autoclaving of pH 5.5. After from about 4 to about 6 months, the somatic embryos are periodically isolated and transferred to the maturation medium described for the high frequency somatic embryogenic pathway. Embryo germination and plantlet development follow the same methodologies as described for the high frequency pathway.

In accordance with the subject invention, it is surprisingly discovered that plants generated by the methods set forth above exhibit a high frequency of variation (see Table 2, Example 3). This result is unexpected since coffee is a tetraploid, and may be attributable to the length of time the cells are in tissue culture.

Tetraploids have four copies of most genes. If one copy is mutated, it may be masked or partially masked by the remaining three normal copies. Coffee regenerates via somatic embryogenesis, not organogenesis. To date, the literature teaches that variation is reduced or non-existent if somatic embryogenesis is the route of regeneration (Hanna et al., Theoret. Appl. Genet. 67:155–159, 1984; Armstrong et al. Planta 164:207–214, 1985; Swedlund et al. Theoret. Appl. Genet. 69:575–581, 1985). Furthermore, as described herein, Ro plants are being selected and hence, all recessive mutants are missed. Accordingly, in consideration of these factors, the subject invention is a significant contribution to the art of somaclonal variation.

Another aspect of this invention relates to in vitro selection before plant regeneration. The term in vitro selection as used herein, refers to the application of a chemical, biological, physical or environmental condition in tissue culture such that somatic embryos are selected favoring one or more characteristics. That is, the conditions in tissue culture are such that certain characteristics possessed by the developing embryos, or parts thereof, are favored to the extent that embryos possessing such characteristics develop into plants with a greater likelihood of being detected. Although not intending to limit the scope of the present invention to one set of applied in vitro conditions, this approach of in vitro selection is exemplified herein by developing embryos in the presence of a caffeine precursor or analog. The range of caffeine-precursors or analogs contemplated by this method includes xanthine 3-N-oxide, 3-methylxanthine, hypoxanthine, 8-chloroxanthine, allopurinol, 7-methylxanthine, 7-methylxanthosine, theobromine, theophylline, xanthine and xanthosine. Use of in vitro selection contemplates recovery of plants with, in the exemplified instance, zero or low levels of caffeine. In the general case, plants exhibiting a variety of properties can be expected. For example, using analogs or precursors of amino acids, fatty acids or pigmentation compounds, following embryogenesis results in plants possessing altered phenotypic properties. The scope of this invention, therefore, relates to the plants, and parts thereof, obtained by regeneration from an explant wherein the media applied to said regeneration may or may not contain metabolic analogs, precursors or inhibitors.

Within the scope of this invention are the plants, and parts thereof, produced by cloning using nodal culture techniques or by growing somatic embryos in bioreactors. In accordance with the teachings of this invention, apical portions of orthotropic shoots bearing from about 4 to about 6 green nodes are washed in 1% (v/v) detergent solution with agitation (150 rpm) and rinsed three times with sterile water. The nodal explants are twice surface sterilized in 1.25% (w/v) sodium hypochlorite for 30 min. The nodal pieces are incubated in a humid chamber overnight before a second sterilization. Individual nodes with an adjacent pair of leaves are cultured by cutting between about half to about two thirds of the leaf blade area and inoculating the explant in a nodal culture medium 5 containing B5 salts, pyridoxine (1–15 $\mu$M), nicotinic acid (1–15 $\mu$M), thiamine (3–30 $\mu$M), meso-inositol (50–550 $\mu$M), cysteine (50–500 $\mu$M), sucrose (87 mM), activated charcoal (2.5 g/l), PVB-40 (1.0 g/l), 6-benzylaminopurine (6-BA) (25–50 $\mu$M), IAA (10 $\mu$M) and agar (7 g/l). The growth conditions employed are the same as those employed for embryo culture during the high frequency pathway previously described.

Every 60 days, the primary shoots are excised and the noded explant transferred to fresh medium. New nodal explants are obtained from in vitro developed shoots.

Before inoculation of a rooting media with the shoots, the shoots can be, but not necessarily have to be, treated by submersion in gibberellic acid (GA) (25–50 ppm). The rooting media comprises: (a) double layer flasks containing basal medium supplemented with IBA (10 $\mu$M) in the top layer and basal medium with added charcoal (2.5 g/l) in the bottom layer; (b) liquid basal medium with IBA (10 $\mu$M) for 10 days followed by paper bridge culture in liquid basal medium; (c) dip the cut end of shoots in a talc preparation containing IBA (10 $\mu$M) and culture in basal solid medium. The nodal cultures are maintained in a growth room under 500 lux illumination with a 14 hr. photoperiod. The development of the arrested orthotropic buds from nodal cultures becomes visible during the third week of culture. The number of developed buds per node varies from about 1 to about 10 and is partially controlled by the level cytokinin. Higher cytokinin levels induce the development of higher numbers of buds, but may cause adverse effects on the subsequent growth of the derived shoots and lower the rooting frequencies. With respect to the cytokinin source, 6-BA has proven more effective than KIN.

In addition to the aforementioned methods, coffee can be micro-propagated by means of embryogenic cell suspensions. This is referred to herein, as high efficiency cloning. This methodology offers the possibility of recovering very high numbers of embryos. Yields of about 100,000 embryos per liter of liquid culture have been obtained. In accordance with this method, embryogenic cell lines are induced from leaf tissues as aforementioned described for the high frequency pathway. Embryogenic cells are then transferred to an embryogenic liquid medium comprising:

Inorganic Salts (mg/l): $NH_4NO_3$ (1,650), $KNO_3$ (1,900), $CaCl_2.2H_2O$ (440), $MgSO_4.7H_2O$ (370), $KH_2PO_4$ (170), $Na_2EDTA$ (37.3), $FeSO_4.7H_2O$ (27.8), $H_3BO_3$ (6.2), $MnSO_4.H_2O$ (16.9), $ZnSO_4.7H_2O$ (8.6), KI (0.83), $Na_2MoO_4.2H_2O$ (0.25), $CuSO_4.5H_2O$ (0.025), $COCl_2.6H_2O$ (0.025).

Amino Acids (mg/l): Glutamine (5.6), Alanine (0.6), Glutamic acid (0.6), Cysteine (0.2), Vitamin-free Casamino acid (250).

Vitamins (mg/l): Inositol (100), Nicotinic acid (1), Pyridoxine.HCl (1), Thiamine HCl (1), D-Calcium pantothenate (1), Folic acid (0.4), p-Aminobenzoic acid (0.02), Biotin (0.01), choline chloride (1.0), Riboflavin (0.2), Ascorbic acid (2.0), Vitamin A (0.01), Vitamin $D_3$ (0.01), Vitamin B12 (0.02)

Other Components: PVP-40 (10 g/l), MES (0.59 mg/l), Sucrose (30 g/l), 2,4-D (1.1 mg/l), and coconut water (50 mg/l).

For example, Erlenmeyer flasks of 125 ml capacity receive 10 ml of the above liquid medium and a small inoculum of embryogenic cells. Periodic inspection of the liquid medium is required for the establishment of a suspension cell line. Coffee embryogenic cells are produced in larger quantities by periodic subcultures of the original culture. Embryogenic cells are then removed from the liquid phase and transferred to a solid media of composition described for the High or Low Frequency pathways. A layer of such cells is then spread on 10$\times$100 mm petri dishes. Once somatic embryos are formed, the aforementioned sequence described for embryo maturation, germination, and plantlet development is followed.

This invention relates to somaclonal variants in coffee generated by the aforementioned plant regenerative techniques. Among the new traits found in accordance with this invention are coffee plants with different patterns of vegetative growth (angle of lateral branches with main axis), differences in leaf shape and size, internode length (short to long internodes; long to short internodes), leaf pigmentation (green to purple), increased and decreased vigor, change in fruit color (red to yellow cherries and yellow to red cherries), fruit morphology and size, early and late maturing, uniform maturation and several different reactions to disease (susceptibility and resistance). Additional somaclonal variants contemplated by this invention include plants with different resistance patterns to cold, drought, caffeine content variability, bean size variability and altered organoleptic properties. The aforementioned variants are described herein as having arisen following short-term variety development.

Coffee plants derived from short-term variety development (somaclonal population or $R_o$ generation) are selected at greenhouse, nursery and field stage of development. The selected individual coffee plants are then submitted to vegetative propagation techniques in order to produce large numbers of each desirable genotype for commercial plantation. Each coffee genotype scaled-up to commercial plantations will constitute a "new coffee variety". This new variety will have a new genotype based on nuclear dominant genes, homozygous nuclear genes, cytoplasmic genes, chromosomal rearrangement, or alteration of chromosomal number.

Medium-term variety development, as defined herein, occurs by submitting the $R_o$ somaclonal population to controlled pollination (also called "selfed"). The resulting $R_1$ population is submitted to new rounds of selection at greenhouse, nursery and field stage of development. The selected plants from this $R_1$ population will be scaled up for commercial production using vegetative methods and seeds derived from controlled pollination (selfing) of individual plants. Each genotype amplified to commercial plantation will constitute a "new coffee variety".

In long-term variety development, each selected $R_1$ somaclonal plant will be selfed and the resulting $R_2$ plants are selected from various stages of development.

Using the methods contained herein, somaclonal variants are obtainable expressing desirable characteristics. These desirable characteristics are divided between those providing agronomical benefits and those providing processing benefits. With respect to desired agronomical traits, those contemplated by the present invention include:

Increased yield potential (select for increased number of flower buds per leaf axil and higher number of green cherries after abscission period)
Higher plant vigor
Faster vegetative growth
Small or large leaf area
Higher net photosynthesis (above 8 mg $CO_2.dm^{-2}.hr^{-1}$)
Shorter maturation cycle (less than 103 weeks for Arabica and less than 116 weeks for Robusta from flowering to mature cherries)
Longer maturation cycle (more than 103 weeks for Arabica and more than 116 weeks for Robusta)
Resistance or tolerance to broad leaf herbicides
Resistance or tolerance to narrow leaf herbicides
Resistance or tolerance to total herbicides
Resistance to drought periods
Resistance to cold temperature
Resistance or tolerance to major coffee diseases (leaf rust, coffee berry disease, Cercospora, Pseudomonas, and Rhizoctonia)
Resistance or tolerance to major insects (coffee borer, leaf miner, nematodes, mealy bugs, Mediterranean fly, and cycads)
Short plant stature (select for short internodes)
Tall plant stature (selected from dwarf plants)
Higher frequency of secondary and tertiary branching
Stronger lateral branches to support heavy cherry load
Cherries with reduced exocarp and mesocarp
Larger bean size
Uniform bean size
Minimal or no pea beans (mokka type)
Male sterile genotypes for hybrid seed production
Presence of trichomes for insect and disease resistance
High efficiency in N, P, K uptake
Tolerance to acid soils and heavy metals
High root/surface ratio
Easy cherry abscission at maturity to facilitate mechanical harvesting With respect to specific cultivars, the agronomic benefit traits contemplated herein include:

Mundo Novo, Icatu and Yellow Bourbon with short stature (semi-dwarf)
Catuai with shorter maturation cycle
Increased uniformity at maturation in Catuai, Caturra, Catimor, Mundo, Novo, and Icatu.
Increased yield of Laurina and Aramosa
Open canopy, longer and stronger lateral branches in Laurina Traits providing processing benefits include:
Higher extractable yield for R & G Coffee
Increased levels of sugars (reducing and non-reducing sugars)
Decreased level of total oils (at 8–10% content)
Increased level of total oils (above 16% content)
Varying levels of caffeine content (0–4%)
Increased level of S-compounds
Increased level of Green Coffee volatiles
Increased total soluble solids for soluble Coffee
Increased amino acid content
Decreased or increased levels of organic acids In a further embodiment, the present invention provides somaclonal variants from *C. arabica* cv. *Laurina* ("Laurina") which are high yielding and low caffeine containing plants obtained in accordance with the methods described herein. These Laurina somaclones produce high cherry yields (relative to Laurina donors which are also herein referred to as "controls") yet retain the low caffeine content characteristic of the Laurina cultivar. Sensorial evaluation indicates the coffee from these Laurina somaclones has the excellent mild Arabica taste. As a group, the high yielding Laurina somaclones have modified morphological characteristics and are more vigorous relative to Laurina donor plants (i.e., the controls). These morphological characteristics include increased leaf area, elongated lateral branches, more cherries per node, increased plant height and more abundant vegetative growth. Additionally, some of these somaclones exhibit heavier single cherries and green beans (on average), and longer internode length. The sugar content of the somaclones varies, however, the oil fraction does not differ significantly from the control plants, indicating that the Laurina somaclones have the commercially desirable oil fraction associated with Arabica varieties (i.e., cultivars).

Seeds representative of the high yielding, low caffeine Laurina somaclone group of the present invention have been deposited with the American Type Culture Collection (ATCC), 12301 Parklawn Drive, Rockville, N. Dak. 20852. These seeds are from the subject *C. arabica* cv. *Laurina* somaclones, are also designated as LS 1992, and have been assigned accession number ATCC -75261.

With respect to yield, the subject Laurina somaclones exhibit an increased yield as measured by cherry weight relative to that obtained from Laurina control plants. Increased cherry yields for individual somaclones have been observed in the range of 118 to 275% relative to the controls. The top 15, 10 and 5 high-yielding Laurina somaclones prepared to date by the method of this invention have a three-year average yield of about 200, 225 and 250% of age-matched controls (See Example 6). Accordingly, high-yielding Laurina somaclones exhibit an increase in total cherry weight relative to the native Laurina plants, i.e. the original genotype explant donors used in producing the subject somaclones. Any high-yielding Laurina somaclone having a cherry weight yield relative to a Laurina control of at least about 115% and up to about 300% or greater is included in this invention. Yield of green coffee beans can also be used as an index to measure increased yield potential or productivity in coffee plants. In this case, the high-yielding Laurina somaclones have an increased green bean yield ranging from at least about 115% and up to about 325% or greater relative to donor controls.

Comparative yields between a high-yielding Laurina somaclone and the native Laurina plants can be determined by method or measure which is indicative of coffee yield, especially as useful to determine commercialization of the coffee product. For example, comparative yields can be demonstrated by measuring the total weight of cherries produce per tree. Alternatively, average yields from several trees can be compared, i.e., either several somaclones or the progeny of a single somaclone can be compared. Cherry weight (kg) obtained per hectare (ha) is another useful measurement for yield determinations. Similar comparisons can be made on a per weight basis for green coffee beans rather than (or in addition to) the cherries. A study published by Carvalho compared total average cherries and green coffee of *C. arabica* cultivars during the period of 1952–1971 and provides general guidelines for comparative yields. (Carvalho, A. in *Coffee: Agronomy* 4:129–165, 1988, Elsevier Applied Sci., London). In that study, the native Laurina cultivar had the lowest cherry yield at 754 kg/ha relative to the other Arabica cultivars which ranged from 854 to 2045 kg/ha. In other words, the other Arabica cultivars produced cherry yields ranging from 113% to 271% greater than Laurina. When green coffee beans were considered in the same study, the other Arabica cultivars produced yields ranging from 149% to 321% relative to Laurina. This study also demonstrates the minimum potential for increased yields obtainable from the Laurina somaclones.

Thus, the yield for the Laurina somaclones of the present invention can range from at least about 113% to 271% or more when ascertained by cherry weight and expressed as kg/ha. Similarly, the yield for the subject Laurina somaclones can range from at least about 149% to 321% or more when ascertained by green coffee and expressed as kg/ha.

As used herein, low caffeine means that the Laurina somaclone has a level of caffeine similar to or lower than that found in the parent Laurina donor plants. Typically, Laurina has about an 0.6%–0.7% caffeine content whereas other Arabica cultivars have an average of about 1.2–1.4% caffeine. Accordingly, low caffeine includes 0.9% caffeine or less including as little as 0.5%, or even fully decaffeinated, i.e., about 0.0 to about 0.1%. Preferably, low caffeine ranges from about 0.5–0.7%. For example, the 15 high yielding, low caffeine Laurina somaclones prepared by this invention have a caffeine content ranging from 0.54% to 0.71%, with an average of 0.62%. Caffeine content can be measured in the plant leaves or green beans according to the method described by Trugo et al. (1989) *Arch. Latinoam. Nutr.* 39:96–107.

The high yielding, low caffeine Laurina somaclones of this invention are prepared by the high frequency or low frequency induction of somatic embryos in accordance with the methods described in detail herein. In particular, these somaclonal variants are generated from an explant of *C. arabic* cv. *Laurina* by culturing the explant for a time and under conditions to induce formation of somatic embryos, culturing the resultant somatic embryos for a time and under conditions sufficient to induce formation of coffee plants by somatic embryogenesis, growing the plants under nursery or field conditions and recovering somaclonal variants by screening the plants for increased coffee yield. Additionally, the somaclones are screened for caffeine content to identify a high-yielding, low caffeine Laurina somaclonal variant in accordance with this invention.

Thus, to identify the Laurina somaclones of the invention the somaclonal plants can be screened at any stage of plant (or plantlet) development. Preferably, the plants are continuously monitored through all stages, especially after moving the plants to nursery or field conditions and observed for those off-parental characteristics which are indicative of high yield. Such screening markers for increased coffee yield for coffee plants include cherry weight, green bean weight, increased number of cherries per node, larger and more abundant leaves, longer lateral branches and more nodes. Moreover, Laurina somaclones which exhibit increased vigor are indicative of plants with higher yield potential. After potentially high-yielding Laurina somaclones are identified by such a screening process, more quantitative yield comparisons can be made, if necessary, as described above with regard to determining cherry weight yields or green coffee yields relative to controls. Thereby, the ordinary skilled artisan can identify high-yielding Laurina somaclones. In addition, the potentially high yielding somaclones are analyzed for caffeine content. These analyses can be conducted at anytime during the screening process for higher yields. Moreover, the screening process can extend over one or more growing seasons and also to the progeny of selected somaclones if desired. The above described screening can be instituted for mass screening of thousands of plants or plantlets as needed.

With respect to agronomical and processing traits, in addition to the traits provided above, those traits further contemplated for the high yielding, low caffeine Laurina somaclones include:

More abundant vegetative growth
Resistance to drought periods
Resistance to cold temperatures
Taller plant stature
Higher frequency of secondary and tertiary branching
Male sterile genotypes for hybrid seed production
Larger leaf size
Presence of trichomes for insect and disease resistance
Easy cherry abscission at maturity to facilitate mechanical harvesting
Increased level of S-compounds to provide an enhance coffee aroma and flavor
Increased level of green coffee volatiles.
Good or extremely good beverage quality as measured by organoleptic analysis.

In a further embodiment, the high-yielding, low caffeine Laurina somaclones can exhibit drought resistance. Such plants retain more leaves, have leaves of darker color, and exhibit relatively higher vigor during drought periods. To obtain one of the subject Laurina somaclones exhibiting drought resistance, the plants are screened or observed during drought periods for characteristics indicative of higher vigor. Accordingly, the invention provides Laurina somaclone LA-2154 which produces a high yield of coffee while retaining the naturally low caffeine content of the parent Laurina cultivar, but having the additional characteristic of drought resistance. This somaclone LA-2154 exhibited drought tolerance during two consecutive years in the field. Seeds from LA-2154 have been deposited with the ATCC and have been assigned accession number ATCC 75262.

The following examples further illustrate the invention.

EXAMPLE 1

Preparation of Solutions

The following solutions are prepared according to the constituents and the respective concentrations listed.

| Constituent | Concentration |
| --- | --- |
| Basal Medium | |
| MS inorganic salts | 1 x |
| Thiamine | 30 μM |
| Cysteine | 210 μM |
| Inositol | 550 μM |
| Sucrose | 117 mM |
| Agar | 8 g/l |
| (for liquid basal medium, the agar is omitted) | |
| Preincubation Medium | |
| MS inorganic salts | 0.5 X |
| Thiamine | 30 μM |
| Cysteine | 210 μM |
| Inositol | 550 μM |
| Sucrose | 87 mM |
| Agar | 8 g/l |
| Maturation Medium | |
| MS inorganic salts | 0.5 X |
| Thiamine | 30 μM |
| Nicotinic acid | 15 μM |
| Pyridoxine | 15 μM |
| Inositol | 550 μM |
| Zeatin or 2-iP | 1.0 PM |
| α-Naphthylacetic acid | 0.25 μM |
| Abscisic acid | 0.25 μM |
| Cysteine | 200 mg/l |
| PVP-40 | 10 g/l |
| Charcoal | 2 g/l |
| Sucrose | 30 g/l |
| Agar | 7 g/l |
| Germination Medium | |
| MS inorganic salts | 0.5 X |
| Thiamine | 30 μM |
| Nicotinic acid | 15 μM |
| Pyridoxine | 15 μM |
| Inositol | 550 μM |
| Sucrose | 20 g/l |
| Zeatin or 2-iP | 2.5 μM |
| Abscisic acid | 0.05 μM |
| Cysteine | 200 mg/l |
| PVP-40 | 10 g/l |
| Gelrite | 2.4 g/l |
| Low Frequency Induction Medium | |
| MS inorganic salts | 1 X |
| Thiamine | 30 μM |
| Nicotinic acid | 15 μM |
| Pyridoxin | 15 μM |
| Cysteine | 200 μM |
| Sucrose | 30 g/l |
| Inositol | 500 μM |
| Zeatin or 2-iP | 10–15 μM |
| 2,4-Dichlorophenoxyacetic acid | 0.5–1.0 μM |
| Agar | 7 g/l |
| Nodal Culture Medium | |
| B5 salts | 1 X |
| Pyridoxine | 15 μM |
| Nicotinic acid | 15 μM |
| Thiamine | 30 μM |
| Meso-Inositol | 550 μM |
| Cysteine | 500 μM |
| Sucrose | 87 mM |
| Activated Charcoal | 2.5 g/l |
| PVP-40 | 1.0 g/l |
| 6-Benzylaminopurine | 25–50 μM |
| Indoleacetic acid | 10 μM |
| Agar | 7 g/l |
| Embryogenic Liquid Medium | |
| $NH_4NO_3$ | 1,650 mg/l |
| $KNO_3$ | 1,900 mg/l |
| $CaCl_2.2H_2O$ | 440 mg/l |
| $MgSO_4.7H_2O$ | 370 mg/l |
| $KH_2PO_4$ | 170 mg/l |

-continued

| Constituent | Concentration |
| --- | --- |
| $Na_2EDTA$ | 37.3 mg/l |
| $FeSO_4.7H_2O$ | 27.8 mg/l |
| $H_3BO_3$ | 6.2 mg/l |
| $MnSO_4.H_2O$ | 16.9 mg/l |
| $ZnSO_4.7H_2O$ | 8.6 mg/l |
| KI | 0.83 mg/l |
| $Na_2MoO_4.2H_2O$ | 0.25 mg/l |
| $CuSO_4.5H_2O$ | 0.025 mg/l |
| $CoCl_2.6H_2O$ | 0.025 mg/l |
| Glutamine | 5.6 mg/l |
| Alanine | 0.6 mg/l |
| Glutamic acid | 0.6 mg/l |
| Cysteine | 0.2 mg/l |
| Vitamin-free Casamino acid | 250 mg/l |
| Inositol | 100 mg/l |
| Nicotinic acid | 1 mg/l |
| Pyridoxine-HCl | 1 mg/l |
| Thiamine HCl | 1 mg/l |
| D-Calcium panthotenate | 1 mg/l |
| Folic acid | 0.4 mg/l |
| p-Aminobenzoic acid | 0.02 mg/l |
| Biotin | 0.01 mg/l |
| Choline chloride | 1.0 mg/l |
| Riboflavin | 0.2 mg/l |
| Ascorbic acid | 2.0 mg/l |
| Vitamin A | 0.01 mg/l |
| Vitamin $D_3$ | 0.01 mg/l |
| Vitamin $B_{12}$ | 0.02 mg/l |
| PVP-40 | 10 g/l |
| MES | 0.59 mg/l |
| Sucrose | 30 g/l |
| 2,4-Dichlorophenoxyacetic acid | 1.1 mg/l |
| Coconut Water | 50 mg/l |

EXAMPLE 2

Coffee Somaclonal Evaluation Field Planting

Each coffee somaclone received a code number at the greenhouse phase (Ex.:CA-115). This code number characterizes a somaclone throughout its experimental life (greenhouse—coffee nursery—coffee field—harvestings—evaluation—cloning).

Coffee somaclones were transferred to a coffee nursery near the plantation site when the somaclones have 2-6 pairs of leaves. The somaclones remained in the nursery until they reached 6"-9" in height when they were transferred to final field location.

Field plantings were made periodically as the coffee somaclones reach the proper size. Somaclones derived from the same genotype (for example, Caturra, Icatu, etc.) were planted in consecutive rows. The field spacing adopted was 3.5 m between rows and 2.0 m between plants and only one plant per hill. At the beginning and at the end of a row of each genotype two control hills with two plants/hill were planted. Each planting was coded and had a different number of plants according to the number of coffee somaclones in the nursery available for field transplanting at a time (Ex.: EC-01 has 500 somaclones; EC-02 has 2,445 somaclones, etc.)

Coffee somaclones received the normal field care recommended for coffee plantations (fertilization, cultivation, fungicide and insecticide). Coffee rows followed the contour path to protect against soil erosion.

Screening Process

Agronomic Characteristics

Twice a year the plants are evaluated for agronomic characteristics. For each genotype within each planting (EC-1, EC-2, etc.), evaluation sheets are made, taking into consideration the following characteristics: phenotype, vegetative growth (grade system from 1–10 representing bad-excellent), stature (tall or short), angle of lateral branched (normal, semi-erect, erect), ploidy (diploid, tetraploid, polyploid, aneuploid), leaf morphology, susceptibility to disease, date of first flowering, flowering load, flowering set (number small beans/no. flower) or abscision frequency, maturity (late, intermediate, or early), uniformity of maturation, cherry color, tolerance to cold, tolerance to drought, weight of mature cherries at 1st, 2nd, and 3rd harvesting, weight of green beans (after processing), and bean size by sieve standards (No. 14–No. 19).

Processing Characteristics

Each somaclone is harvested individually and only mature cherries are collected. Several harvestings are made in order to collect all mature cherries on each plant. Mature cherries are weighed, washed, depulped, and fermented. After mucilage is removed by fermentation, coffee seeds are washed and pre-dried under forced-air tunnel followed by hot-air tunnel until reaching 11–13% seed moisture. Parchment is removed from coffee seeds and each somaclone is submitted to a series of analytical tests that are relevant for the coffee processing industry. Sensory analysis with an organoleptic description is made for the most interesting somaclones.

Table 1 lists somaclonal variant types obtained by employing the respective procedures disclosed herein and using the solutions listed in Example 1.

TABLE 1
Data of Selected Variant Types of Coffee

| Variant Type | Somaclone Number | Regeneration Pathway HF[1]/LF[2] | Period in Culture Medium (Months) |
|---|---|---|---|
| Change in fruit color: red to yellow | CA-115[3] | LF | 13 |
| | CA-169 | HF | 13 |
| | CA-311 | LF | 14 |
| | CA-377 | HF | 14 |
| | CA-410 | LF | 14 |
| | CA-420 | LF | 15 |
| Reversion from short to long internode | CTY-1785[4] | LF | 31 |
| | CTY-1789 | LF | 31 |
| | CTY-1790 | HF | 32 |
| | CTY-1791 | HF | 33 |
| | CTY-1799 | HF | 33 |
| | CR-1616[5] | LF | 26 |
| | CR-1130 | LF | 27 |
| | CR-1783 | LF | 27 |
| | CR-1786 | LF | 27 |
| | CR-1787 | LF | 27 |
| | CR-1798 | LF | 29 |
| | CTR-245[6] | LF | 12 |
| | CTR-294 | HF | 16 |
| | CTR-323 | HF | 16 |
| | CTR-935 | | |
| | CTR-1062 | HF | 23 |
| | CA-116 | HF | 16 |
| Mutation to short internodes | IC-1867[7] | LF | 14 |
| | IC-2150 | LF | 16 |
| | IC-2266 | LF | 16 |
| | IC-2267 | LF | 16 |
| | IC-2504 | LF | 13 |
| | IC-2505 | LF | 13 |
| | IC-2704 | LF | 15 |
| | IC-2907 | LF | 15 |
| | IC-82 | LF | 15 |
| Susceptible to ants | CTR-1014 | | |
| Polyploids | CA-720 | | |
| Different architecture | LA-2051[8] | LF | 12 |
| | LA-2253 | LF | 14 |
| | LA-2255 | LF | 14 |
| | LA-2378 | LF | 15 |
| | LA-2480 | LF | 15 |
| | LA-2574 | LF | 16 |

TABLE 1-continued
Data of Selected Variant Types of Coffee

| Variant Type | Somaclone Number | Regeneration Pathway HF[1]/LF[2] | Period in Culture Medium (Months) |
|---|---|---|---|
| | LA-3159 | LF | 18 |

[1]HF: High Frequency Pathway
[2]LF: Low Frequency Pathway
[3]CA: *Coffea arabica* cv. Caturra
[4]CTY: *Coffea arabica* cv. Yellow Catuai
[5]CR: *Coffea arabica* cv. Catimor
[6]CTR: *Coffea arabica* cv. Red Catuai
[7]IC: *Coffea arabica* cv. Icatu
[8]LA: *Coffea arabica* cv. Laurina

EXAMPLE 3

Somaclonal Variability

Table 2 lists the frequency of variablility of different varieties of coffee employed herein to produce somaclonal variants.

TABLE 2

| Variety of Coffee | Frequency of Variability | | |
|---|---|---|---|
| | No. Plants in Field | No. Plants with Variation | Frequency of Variability |
| Caturra | 96 | 7 | 7 |
| Yellow Catuai | 229 | 5 | 2 |
| Catimor | 1 | 1 | 100 |
| Icatu | 580 | 9 | 2 |
| Laurina | 106 | 7 | 7 |

EXAMPLE 4

Somaclonal Variant Field Data

Table 3 lists field data from selected somaclonal variants obtained in accordance with the respective procedure employed herein.

TABLE 3
Field Data of Selected Somaclonal Variants

| Somaclone Number | Variety | Field Evaluation | Regen. Pathway HF/LF |
|---|---|---|---|
| CA-45 | Caturra | | |
| CA-61 | Caturra | Vigor 3[1] | HF |
| CA-951 | Caturra | Vigor 3 | |
| CA-362 | Caturra | Vigor 2, Open architecture[2] more lateral branches | HF |
| CA-40 | Caturra | Vigor 1 | HF |
| CA-636 | Caturra | Vigor 1 | |
| CA-967 | Caturra | Vigor 1 | |
| CA-303 | Caturra | Vigor 1, many fruits, different architecture | HF |
| CA-365 | Caturra | Vigor 1, short plant | HF |
| CA-223 | Caturra | Vigor 1 | LF |
| CA-640 | Caturra | Vigor 1 | |
| CA-495 | Caturra | Vigor 1 | |
| CA-602 | Caturra | Vigor 1 | |
| CA-115 | Caturra | Red to yellow fruits | LF |
| CA-169 | Caturra | Red to yellow fruits | HF |
| CA-311 | Caturra | Red to yellow fruits | LF |
| CA-377 | Caturra | Red to yellow fruits | HF |
| CA-410 | Caturra | Red to yellow fruits | LF |
| CA-420 | Caturra | Red to yellow fruits | LF |
| CA-16 | Caturra | Angustifolia,[3] short internodes | LF |
| CA-19 | Caturra | Angustifolia | LF |
| CA-18 | Caturra | Angustifolia | LF |
| CA-325 | Caturra | Open architecture, more secondary lateral branches, leaves darker and thicker | LF |
| CA-220 | Caturra | Open architecture, die back | HF |
| CA-395 | Caturra | Open architecture, narrow leaves, less heavy leaves, folds up | LF |

TABLE 3-continued
Field Data of Selected Somaclonal Variants

| Somaclone Number | Variety | Field Evaluation | Regen. Pathway HF/LF |
|---|---|---|---|
| CA-961 | Caturra | Open architecture | |
| CA-152 | Caturra | Open architecture | HF |
| CA-5 | Caturra | Die-back,[4] susceptible P. garcae[5] | LF |
| CA-903 | Caturra | Die-back, susceptible P. garcae | |
| CA-97 | Caturra | Die-back, susceptible P. garcae | LF |
| CA-680 | Caturra | Die-back, susceptible P. garcae | |
| CA-168 | Caturra | Die-back, susceptible P. garcae | HF |
| CA-98 | Caturra | Die-back, susceptible P. garcae | LF |
| CA-265 | Caturra | Die-back, susceptible P. garcae | HF |
| CA-469 | Caturra | Die-back, susceptible P. garcae | |
| CA-502 | Caturra | Die-back, susceptible P. garcae | |
| CA-927 | Caturra | Die-back, susceptible P. garcae | |
| CA-158 | Caturra | Susceptible P. garcae | HF |
| CA-1030 | Caturra | Susceptible P. garcae | |
| CA-198 | Caturra | Dwarf stature | HF |
| CA-289 | Caturra | Dwarf stature, off type leaf | HF |
| CA-741 | Caturra | Dwarf stature | |
| CA-405 | Caturra | Early maturing, 70% red fruits | LF |
| CA-654 | Caturra | Narrow leaves (Typica type,[6] less heavy, pale green color[7] | |
| CTR-323 | Red Catuai | Reversion too long, internode, high yield, heavy flower buds | HF |
| CTR-294 | Red Catuai | Reversion too long, internode | HF |
| CTR-245 | Red Catuai | Reversion too long, internode purpuracens, flat leaves | LF |
| TR-394 | Red Catuai | Vigor 2 | HF |
| CTR-341 | Red Catuai | Vigor 1 | HF |
| CTR-347 | Red Catuai | Vigor 1 | HF |
| CTR-704 | Red Catuai | Vigor 1 | |
| CTR-1014 | Red Catuai | Susceptible to ants | |
| CTY-186 | Yellow Catuai | Vigor 3, heavy fruit load | HF |
| CTY-349 | Yellow Catuai | Vigor 3, heavy fruit load | LF |
| CTY-359 | Yellow Catuai | Vigor 3 | HF |
| CTY-144 | Yellow Catuai | Vigor 1, smaller leaves, fold | HF |
| CTY-705 | Yellow Catuai | Vigor 1 | |
| CTY-117 | Yellow Catuai | Vigor 1 | HF |
| CTY-373 | Yellow Catuai | Twisted petiole | LF |
| CTY-918 | Yellow Catuai | Susceptible to ants | |
| CTY-105 | Yellow Catuai | Susceptible to ants | LF |
| IC-82 | Icatu | Vigor 3, short internodes (CT mutant), dark green leaves, resistant to P. garcae and leaf miner | LF |
| IC-391 | Icatu | Vigor 3, potentially high yield | HF |
| T-9[8] | Typica | Vigor 1 | HF |
| T-88 | Typica | Vigor 1 | HF |
| T-4 | Typica | Vigor 1 | HF |
| T-12 | Typica | Vigor 1 | HF |
| T-257 | Typica | Vigor 1 | HF |
| CA-206 | Caturra | Vigor 3 | |
| CA-890 | Caturra | Angustifolia | |
| CA-523 | Caturra | Angustifolia | |
| CA-904 | Caturra | Angustifolia | |
| CA-894 | Caturra | Angustifolia | |
| CA-532 | Caturra | Angustifolia | |
| CA-523 | Caturra | Angustifolia, purpuracens | |
| CA-891 | Caturra | Angustifolia | |
| CA-894 | Caturra | Angustifolia, dwarf plant | |
| CA-888 | Caturra | Angustifolia, dwarf plant | |
| CA-116 | Caturra | Reversion to long internodes | HF |
| CA-1694 | Caturra | Poor growth, short plant | HF |
| CA-720 | Caturra | Polyploide, thick leaves and different morphology | |
| CA-880 | Caturra | Disease resistant | |
| CA-516 | Caturra | Disease resistant | |
| CA-826 | Caturra | Susc.[9] disease-rust/P. garcae/cold | |
| CA-838 | Caturra | Susc. P. garcae | |
| CA-1037 | Caturra | Susc. P. garcae | |
| CA-852 | Caturra | Cold | |
| CA-543 | Caturra | Susc. P. garcae | |
| CA-1244 | Caturra | Susc. P. garcae | |
| CR-1616 | Catimor | Reversion to long internodes | LF |
| CR-1730 | Catimor | Reversion to long internodes | LF |
| CR-1783 | Catimor | Reversion to long internodes | LF |
| CR-1786 | Catimor | Reversion to long internodes | LF |
| CR-1787 | Catimor | Reversion to long internodes | LF |
| CR-1798 | Catimor | Reversion to long internodes | LF |
| CR-2854 | Catimor | Vigor 3 | LF |
| CR-2569 | Catimor | Vigor 3 | LF |
| CR-1620 | Catimor | Vigor 3 | LF |
| CR-2112 | Catimor | Vigor 3 | LF |
| CR-1870 | Catimor | Poor growth | LF |
| CR-1840 | Catimor | Poor growth | LF |
| IC-1851 | Icatu | Architecture | LF |
| IC-1867 | Icatu | Mutation to short internodes (CT), narrow leaves | LF |
| IC-2150 | Icatu | Mutation to short internodes (CT) | LF |
| IC-2266 | Icatu | Mutation to short internodes (CT) | LF |
| IC-2267 | Icatu | Mutation to short internodes (CT) | LF |
| IC-2504 | Icatu | Mutation to short internodes (CT) | LF |
| IC-2505 | Icatu | Mutation to short internodes (CT) | LF |
| IC-2704 | Icatu | Mutation to short internodes (CT) | LF |
| IC-2907 | Icatu | Mutation to short internodes (CT), purpur[10] leaves | LF |
| IC-2733 | Icatu | Vigor 3, dark green leaves | LF |
| IC-2505 | Icatu | Vigor 3 (best), dark green, purpur leaves | LF |
| IC-2504 | Icatu | Vigor 3 (best,), dark green, purpur leaves | LF |
| IC-2330 | Icatu | Vigor 2, dark leaves, purp | LF |
| IC-2522 | Icatu | Robusta leaf type | LF |
| IC-2251 | Icatu | Robusta leaf type | LF |
| IC-2904 | Icatu | Robusta leaf type | LF |
| IC-1815 | Icatu | Poor growth | LF |
| IC-1826 | Icatu | Poor growth, very small plant | HF |
| IC-1881 | Icatu | Poor growth, very small plant | LF |
| IC-2024 | Icatu | Poor growth, very short plant | LF |
| IC-2986 | Icatu | Purpur. leaves | LF |
| IC-4126 | Icatu | Purpur. leaves | HF |
| IC-3224 | Icatu | Dark green leaves, purpur. | LF |
| IC-2974 | Icatu | Dark green leaves, purpur. | LF |
| IC-2464 | Icatu | Green-yellow leaves (all plant leaves | LF |
| IC-2476 | Icatu | Mealybugs | LF |
| IC-1065 | Icatu | Disease susc. purp. | HF |
| CTY-421 | Yellow Catuai | Different architecture (½) tighter angles, more compact | HF |
| CTY-1785 | Yellow Catuai | Reversion to long internode | LF |
| CTY-1789 | Yellow Catuai | Reversion to long internode | LF |
| CTY-1790 | Yellow Catuai | Reversion to long internode | HF |
| CTY-1791 | Yellow Catuai | Reversion to long internode | HF |
| CTY-1799 | Yellow Catuai | Reversion to long internode | HF |
| CTY-724 | Yellow Catuai | Vigor 3 | |
| CTY-478 | Yellow Catuai | Vigor 3 | |

TABLE 3-continued

Field Data of Selected Somaclonal Variants

| Somaclone Number | Variety | Field Evaluation | Regen. Pathway HF/LF |
|---|---|---|---|
| CTY-701 | Yellow Catuai | Vigor 3 | |
| CTY-1058 | Yellow Catuai | Vigor 2 | HF |
| CTY-913 | Yellow Catuai | Vigor 2 | |
| CTY-921 | Yellow Catuai | Vigor 1 | |
| CTY-451 | Yellow Catuai | Vigor 1 | |
| CTY-1214 | Yellow Catuai | Vigor 1 | HF |
| CTY-1217 | Yellow Catuai | Poor Growth | HF |
| CTY-1094 | Yellow Catuai | Poor growth (very short plant) | HF |
| CTY-1632 | Yellow Catuai | Poor growth (very short plant) | HF |
| CTY-1093 | Yellow Catuai | very poor growth | HF |
| CTY-491 | Yellow Catuai | Susc. P. garcae | |
| CTY-1451 | Yellow Catuai | Susc. P. garcae | HF |
| CTY-1019 | Yellow Catuai | Susc. P. garcae | |
| CTY-593 | Yellow Catuai | Mealybugs & Fumagina[11] | |
| CTR-2067 | Red Catuai | Vigor 3 | LF |
| CTR-1114 | Red Catuai | Vigor 3, presence Mealybug | |
| CTR-935 | Red Catuai | Reversion to long internode | |
| CTR-1062 | Red Catuai | Reversion to long internode | HF |
| CTR-2653 | Red Catuai | Purpuracen | HF |
| CTR-3007 | Red Catuai | Different architecture | HF |
| CTR-3941 | Red Catuai | Very poor growth | LF |
| CTR-1852 | Red Catuai | Poor growth, narrow leaves very susc. P. garcae | HF |
| CTR-1120 | Red Catuai | Poor growth | HF |
| CTR-862 | Red Catuai | Poor growth, susc. P. garcae | |
| CTR-1875 | Red Catuai | Poor growth, different leaf morphology | HF |
| CTR-2043 | Red Catuai | Poor growth (ca. 6" tall only) | LF |
| CTR-1966 | Red Catuai | Poor growth | LF |
| CTR-1602 | Red Catuai | Narrow leaves, smaller leaf area, very short internodes | HF |
| LA-2051 | Laurina | Different architecture, broader leaves | LF |
| LA-2253 | Laurina | Different architecture, broader leaves, short internodes | LF |
| LA-2255 | Laurina | Different architecture, Vigor 3, broader leaves | LF |
| LA-2378 | Laurina | Different architecture, broader leaves, Millibug | LF |
| LA-2480 | Laurina | Different architecture, broader leaves | LF |
| LA-2574 | Laurina | Different architecture, broader leaves | LF |
| LA-3159 | Laurina | Different architecture, broader leaves, purpur. | LF |
| T-2180 | Typica | Smaller leaf area (50% reduction) | HF |

[1]Vigor 3: excellent vegetative growth; Vigor 2: normal vegetative growth; Vigor 1: below normal vegetative growth.
[2]Architecture: denotes a change from the normal plant architecture recognized for a particular genotype.
[3]Augustifolia: Abnormal leaf morphology (elongated) and smaller leaf area than normal plant.
[4]Die-back: Tissue dies off from tip. Associated with bad vigor and Colletrotrichum infection.
[5]*Pseudononas. garcae* (high altitude infecting agent).
[6]Typica type: old arabica type.
[7]Relative to wild type.
[8]T: *Coffea arabica* cv. Typica
[9]Susc: susceptible
[10]purpur: purpuracens (contains anthocyanin in leaves).
[11]Fumagina: fungus Secondary infection from Mealybugs

EXAMPLE 5

Coffee somaclones were produced and shipped to a Coffee Experimental Farm located in a prime coffee growing region in the State of São Paulo, Brazil. A total of 15,593 somaclones were transferred to field conditions at different planting dates and they were evaluated as they reached maturity (Tables 4A, 4B and 4C).

Table 4A shows the percentage of variability observed in the somaclones produced from several *C. arabica* cultivars. The variability, i.e. the number of mutations observed, range from 3.1% (Arabica typica) to 39.0% (Laurina) with an overall average variability of 9.8%.

Tables 4B and 4C illustrate the frequency with which different morphological and physiological traits, i.e. observed phenotypes, appeared in the total population of somaclones planted in field trials. Certain phenotypic variations were observed at high frequency such as conversion form Laurina to Arabica (31.5%), change of bean color from yellow to red (42.4%), lethality (13.9%), change from tall stature to short stature (3.8%) and production of small beans (2.7%).

At harvest, the somaclone plants were evaluated for morphological and physiological characteristics that diverged from the control donor plants. At that time, a total of 12,167 somaclone plants were evaluated at least once under field conditions (Table 4B). The most common mutations observed were cherry color (yellow to red, or red to yellow), plant height (tall to short stature or short to tall stature), leaf morphology (elongated, size, smooth surface, etc.), and overall plant architecture (shape). Other mutations include anthocyanin production (purpuracens), cherry morphology (elongated, pear shape, round shape), Maragogype mutation (very large fruits and leaves), and the presence of polyploids and aneuploidies. The somaclones that did not survive after 1-2 years under field conditions were considered lethal variants. The reported lethal variants do not include somaclone plants that were eliminated due to transplanting (first 6 months), cold fronts (4-6 months afterwards), and/or drought (4-6 month period). All these morphological mutants have been stable from year to year under field conditions. Some of the somaclones have expressed known genetic markers; (like short stature, cherry color, purpuracens, maragogype, etc.) however, these mutations have been induced by the somaclone process in a different genetic background relative to the usual varieties which express these markers (e.g., high yielding commercial Arabica varieties).

Another group of variants was identified as early or late maturing, uniform maturing, uncontrolled flowering (semperflores), more susceptible or resistant to diseases, and different bean size (Table 4C). These characteristics are affected by environmental conditions and so may vary from year to year. Ongoing observations are being made in consecutive years to determine if expression of these traits is independent of the growth conditions.

TABLE 4A

Coffee Somaclones. Number of Mutations by Genotype Observed in Field Evaluations

| Genotype[1] | Total Mutations | Total Evaluated | % Variability |
|---|---|---|---|
| CA | 193 | 879 | 22.0 |
| CTY | 99 | 444 | 22.3 |
| CTR | 140 | 4275 | 3.3 |
| LA | 172 | 441 | 39.0 |
| CR | 197 | 2061 | 9.6 |
| IC | 197 | 2243 | 8.8 |
| MN | 110 | 1253 | 8.8 |
| AR | 10 | 325 | 3.1 |
| YB | 78 | 255 | 30.6 |
| Totals | 1196 | 12176 | 9.8 |

[1]Genotype abbreviations for these varieties are as follows: CA, Caturra; CTR, Red Catuai; CR, Catimor; IC, Icatu; LA, Laurina; CTY, Yellow Catuai; MN, Mundo Novo; AR, Arabica typica; YB, Yellow Bourbon

TABLE 4B

Variability of Coffee Somaclone: Morohological and Single Gene Traits

| Classes of Variation | Total No. Somaclones Evaluated | Total No. Mutated Somaclones | Presumed Genotype | Variation Frequency (%) |
|---|---|---|---|---|
| Tall to Short | 3724 | 140 | Ct/— | 3.76 |
| Short to Tall | 8416 | 107 | ct ct | 1.27 |
| Arabica to Laurina | 11726 | 12 | lr lr | 0.10 |
| Laurina to Arabica | 441 | 139 | Lr/— | 31.52 |
| Leaf Morphology | 12167 | 160 | | 1.32 |
| Purpuracens | 12167 | 32 | pr pr | 0.26 |
| Cherry Morphology | 12167 | 20 | | 0.16 |
| Red to Yellow Beans | 11468 | 134 | xc xc | 1.17 |
| Yellow to Red Beans | 699 | 296 | Xc/— | 42.35 |
| Maragogype | 12167 | 1 | Mg/— | 0.01 |
| Polyploids | 12167 | 9 | 8x | 0.07 |
| Aneuploids | 12167 | 77 | | 0.63 |
| Sectorial Chimera | 12167 | 1 | | 0.01 |
| Plant Architecture | 12167 | 185 | | 1.52 |
| Lethal (Dead) | 12167 | 1686 | | 13.86 |

TABLE 4C

Variability of Coffee Somaclones: Physiological and Quantitative Characters

| Classes of Variation | Total No. Somaclones Evaluated | Total No. Mutated Somaclones | Variation Frequency (%) |
|---|---|---|---|
| Early Maturing | 12167 | 6 | 0.05 |
| Late Maturing | 12167 | 33 | 0.27 |
| Uniform Maturing | 12167 | 4 | 0.03 |
| Semperflores | 12167 | 27 | 0.22 |
| Ant Susceptible | 12167 | 28 | 0.23 |
| Disease Susceptible | 12167 | 88 | 0.72 |
| Disease Resistant | 12167 | 9 | 0.07 |
| Large Beans (#18)[a] | 7504 | 89 | 1.19 |
| Small Beans (#14)[b] | 7504 | 201 | 2.68 |

[a]retained by sieve size #18
[b]retained by sieve size #14

Example 6

High Yielding Laurina Somaclones: Yield Potential

The top 15 Laurina somaclones during 1989–1991 produced a three-year average yield of 3005 g cherries (max.=4120 g; min=1767 g) whereas the equivalent average yield for Laurina controls was 1498 g (Table 5A). If the top 10 high-yielding Laurina somaclones are considered, the three-year average is 3395 g cherries, i.e. more than twice (2.3×) the average cherry yield of control plants (Table 5B). The cherry yield of the top five high-yielding Laurina somaclones has a three-year average of 3746 g, i.e. approximately 2.5 times the control value (Table 5C). Statistical analysis indicates that the individual somaclones LA-3063, 2444, 2296, 2168, 2165 and 2154 are different from the control at a 95% confidence level. Statistical analysis for all data was performed using the STATPAK program and comparing the data based on the confidence limits (at 95%) for a t-distribution in accordance with Snedecor et al. (1967) *Statistical Methods* 6th Ed., Ames, Iowa.

When the average yield of the top 15 selected somaclones is compared with the control average yield, it demonstrates that this group of high yielding Laurina plants produce higher yields at significant levels (at 95%) relative to the original donor genotypes. Similar statistically significant differences hold when the yield average of the top 10 or the top 5 high yielding Laurina somaclones is considered.

The vigor rating of the high yielding, low caffeine Laurina somaclones is also provided in Table 5A–C.

The vigor grade uses a scale of 1 to 10 in which grade 10 is the maximum and grade 1 the minimum value. This vigor scale is based on vegetative growth (presence of leaves, lateral branching, plant height, diameter of stem, diameter of canopy, etc.) and fruit load. The maximum grade (10) is attributed to a plant with maximum fruit load and very abundant vegetative growth. Such vigor grading system is extensively used by coffee breeders to make field selections of segregating progenies as described by Carvalho et al. (1959) *Bragantia, Campinas* 18: 373–386; Carvalho et al. (1984) *Bragantia, Campinas* 43: 509–517; Fernie (1965) *Coffee breeding in tanganyika*, FAO report, Rio de Janeiro; and Fazuoli, L. C. (1991) *Methods, criteria and selection data in progenies of Icatu coffee with resistance to Hemileria vastatrix*. Doctoral dissertation, UNICAMP, Campinas, Brazil.

Hence, there are Laurina somaclones with higher three year average yield and vegetative vigor than the Laurina control plants. Closer analysis of these high yielding Laurina somaclones revealed that they have modified morphological characteristics in comparison to the native donor genotypes. These morphological characteristics appear to be influencing the total yield output of the subject Laurina somaclones. Such observed characteristics include increased leaf area, elongate lateral branches, higher number of cherries per node, and increased plant height.

In summary, the field testing of these high-yielding Laurina somaclones after 3-4 years of continuous evaluation demonstrated that their unique phenotypes have been stable throughout multiple growing and harvesting seasons as shown in the Examples herein. Therefore, these Laurina somaclones carry stable genetic changes that were not reversible during the growth cycle of the plants under normal field conditions.

TABLE 5A

Yield data for the 15 selected High Yielding Laurina Somaclones and Laurina controls for 1989, 1990 and 1991 harvests

| Genotype | Somaclone Number | Plant Vigor 1991 | Cherry Weight 1991 (g) | Cherry Weight 1990 (g) | Cherry Weight 1989 (g) | Average Cherry Wt (3 years) (g) | % Control |
|---|---|---|---|---|---|---|---|
| LA | 2154 | 10 | 3040 | 5850 | 1350 | 3413* | 228 |
| LA | 2165 | 8 | 6800 | 4330 | 1230 | 4120* | 275 |
| LA | 2167 | 9 | 4700 | 4070 | 940 | 3237 | 216 |
| LA | 2168 | 7 | 4440 | 2720 | 3440 | 3533* | 236 |
| LA | 2184 | 8 | 3050 | 2940 | 1120 | 2370 | 158 |
| LA | 2213 | 9 | 1390 | 4770 | 1450 | 2537 | 169 |
| LA | 2229 | 7 | 2500 | 4250 | 1080 | 2610 | 174 |
| LA | 2295 | 9 | 2190 | 2990 | 1960 | 2380 | 159 |
| LA | 2296 | 8 | 3320 | 4860 | 2330 | 3503* | 234 |
| LA | 2392 | 9 | 3730 | 4140 | 220 | 2697 | 180 |
| LA | 2444 | 8 | 6580 | 3770 | 430 | 3593* | 240 |
| LA | 2575 | 9 | 5020 | 3380 | 1390 | 3263 | 218 |
| LA | 2576 | 9 | 1300 | 3340 | 660 | 1767 | 118 |
| LA | 2589 | 8 | 2050 | 3830 | 320 | 2067 | 138 |
| LA | 3063 | 8 | 4150 | 4050 | 3740 | 3980* | 266 |
| Average | | | 3617 | 3953 | 1444 | 3005* | 201 |
| STD | | | 1629 | 800 | 1008 | 708 | |
| Control | | | 1607 | 1524 | 700 | 1498 | — |
| STD | | | 1109 | 784 | — | 937 | |

Abbreviations for Tables 5-15: Avg, average; LA, Laurina; ND, not determined; STD, standard deviation of the mean; wt, weight.
*for Tables 5-15: LSD 95%.

TABLE 5B

Yield data for the Top 10 High Yielding Laurina Somaclones and Laurina controls for 1989, 1990 and 1991 harvests

| Genotype | Somaclone Number | Plant Vigor 1991 | Cherry Weight 1991 (g) | Cherry Weight 1990 (g) | Cherry Weight 1989 (g) | Average Cherry Wt (3 years) (g) | % Control |
|---|---|---|---|---|---|---|---|
| LA | 2154 | 10 | 3040 | 5850 | 1350 | 3413* | 228 |
| LA | 2165 | 8 | 6800 | 4330 | 1230 | 4120* | 275 |
| LA | 2167 | 9 | 4700 | 4070 | 940 | 3237 | 216 |
| LA | 2168 | 7 | 4440 | 2720 | 3440 | 3533* | 236 |
| LA | 2229 | 7 | 2500 | 4250 | 1080 | 2610 | 174 |
| LA | 2296 | 8 | 3320 | 4860 | 2330 | 3503* | 234 |
| LA | 2392 | 9 | 3730 | 4140 | 220 | 2697 | 180 |
| LA | 2444 | 8 | 6580 | 3770 | 430 | 3593* | 240 |
| LA | 2575 | 9 | 5020 | 3380 | 1390 | 3263 | 218 |
| LA | 3063 | 8 | 4150 | 4050 | 3740 | 3980* | 266 |
| Average | | | 4428 | 4142 | 1615 | 3395* | 227 |
| STD | | | 1346 | 789 | 1127 | 481 | |
| Control | | | 1607 | 1524 | 700 | 1498 | — |
| STD | | | 1109 | 784 | — | 937 | |

TABLE 5C

Yield data for the Top 5 High Yielding Laurina Somaclones and Laurina controls for 1989, 1990 and 1991 harvests

| Genotype | Somaclone Number | Plant Vigor 1991 | Cherry Weight 1991 (g) | Cherry Weight 1990 (g) | Cherry Weight 1989 (g) | Average Cherry Wt (3 years) (g) | % Control |
|---|---|---|---|---|---|---|---|
| LA | 2165 | 8 | 6800 | 4330 | 1230 | 4120* | 275 |
| LA | 2168 | 7 | 4440 | 2720 | 3440 | 3533* | 236 |
| LA | 2296 | 8 | 3320 | 4860 | 2330 | 3503* | 234 |
| LA | 2444 | 8 | 6580 | 3770 | 430 | 3593* | 240 |
| LA | 3063 | 8 | 4150 | 4050 | 3740 | 3980* | 266 |

TABLE 5C-continued

Yield data for the Top 5 High Yielding
Laurina Somaclones and Laurina controls
for 1989, 1990 and 1991 harvests

| Genotype | Somaclone Number | Plant Vigor 1991 | Cherry Weight 1991 (g) | Cherry Weight 1990 (g) | Cherry Weight 1989 (g) | Average Cherry Wt (3 years) (g) | % Control |
|---|---|---|---|---|---|---|---|
| Average | | | 5058 | 3946 | 2234 | 3746* | 251 |
| STD | | | 1384 | 711 | 1264 | 284 | |
| Control | | | 1607 | 1524 | 700 | 1498 | — |
| STD | | | 1109 | 784 | — | 937 | |

EXAMPLE 7

High Yielding Laurina Somaclones: Morphology

A. Leaf Area

The leaf area of each high-yielding Laurina somaclonal and control plants was evaluated in April 1991, just before harvesting. The leaf area data show that 13 individual Laurina somaclone plants from this group have higher leaf area than the control at the 95% confidence limit (Table 6). When the average leaf area for the group of 15 somaclones is considered, the leaf area value is different from the control at 95% confidence.

B. Cherry Weight and Green Bean Weight

The weight of single cherries and green beans were evaluated for each of the 15 Laurina somaclone plant of the high-yielding group (Table 7). Seven individual somaclones had higher cherry weight than the control plants and 13 individual somaclones had heavier beans than the controls (at 95% limit of confidence). The average cherry weight for the group of 15 selected Laurina somaclones is also significantly different from the control cherry weight. The ratio of cherry weight to green bean weight oscillated between 7:1 to 9:1 for the somaclone plants. The smaller this ratio is, the larger the bean size relative to the cherry. The control plants show a ratio of 9:1 (Table 7).

C. Length of Lateral Branches

Another factor for higher yield in coffee is the length of lateral branches since coffee cherries are only produced in the leaf axils of these branches. Hence, the high yielding somaclones which were measured (14 of 15) had larger lateral branches than the original Laurina donor plants at 95% limit of confidence (Table 8).

D. Internode Length

The measurement of internode length of the lateral branches from the 15 selected high-yielding Laurina somaclone showed that 11 individual somaclones have longer internode length than donor plants at a 95% limit of confidence (Table 9). The average internode length for the 15 selected somaclones (1.97 cm) is also significantly different from the internode length of the control plants (1.55 cm).

Longer lateral branches can be explained by increased number of nodes, by increased length of the internodes, or both parameters simultaneously. In these selected Laurina somaclones, longer lateral branches are explained by longer internodes (Table 9). Hence, this morphological feature reflects a more vigorous vegetative growth of the selected Laurina somaclones relative to the control Laurina plants. There is also an increase in the total number of cherries per lateral branch. Longer lateral branches among most of the Laurina somaclones is a consequence of higher vegetative growth in comparison with control plants.

E. Plant Height, Top and Bottom Width

The average height of the 15 high-yielding somacloned was statistically higher (1.90 m) than the average control plants (1.58 m). Measurements of width at the top and bottom of the selected Laurina somaclone plants also show that the somaclone plants had a larger vegetative growth than the control donor genotype (Table 10).

F. Number of Cherries Per Node

The increased yield from the 15 selected Laurina somaclones could be explained by an increased number of nodes, or by an increase in the number of cherries per node, or both. Hence, the number of cherries per node were evaluated for ten branches per somaclone and donor control plant (Table 11). Nine individual somaclones had a higher number of cherries per node in comparison to control (at 95% confidence limit). When the average number of cherries from all 15 Laurina somaclones is considered, the average number is still statistically distinct from the control number.

TABLE 6

Leaf area of the 15 selected High Yielding
Laurina Somaclones and Laurina controls
evaluated in April 1991

| Genotype | Somaclone Number | Leaf Area ($mm^2$) Average | STD |
|---|---|---|---|
| LA | 2154 | 11.81* | .12 |
| LA | 2165 | 10.57* | .48 |
| LA | 2167 | 11.83* | .17 |
| LA | 2168 | 9.66 | .23 |
| LA | 2184 | 8.05 | .15 |
| LA | 2213 | 14.00* | .54 |
| LA | 2229 | 13.00* | .54 |
| LA | 2295 | 13.33* | .40 |
| LA | 2296 | 12.34* | .09 |
| LA | 2392 | 14.15* | .54 |
| LA | 2444 | 11.59* | .19 |
| LA | 2575 | 11.07* | .34 |
| LA | 2576 | 10.56* | .20 |
| LA | 2589 | 12.52* | .84 |
| LA | 3063 | 10.83* | .29 |
| Average | | 11.69* | .34 |
| Control | | 8.67 | .57 |

TABLE 7

Comparative Cherry weight and green bean
weight per fruit for the 15 selected High
Yielding Laurina Somaclones and Laurina
controls from 1991 crop

| Genotype | Somaclone[a] Number | Cherry Weight (g) | STD | Green Weight (g) | STD | Ratio Cherry Weight/ Green Bean Wt. |
|---|---|---|---|---|---|---|
| LA | 2154 | 1.450* | .040 | .167* | .008 | 9:1 |
| LA | 2165 | 1.440 | .030 | .167* | .013 | 9:1 |
| LA | 2167 | 1.480* | .050 | .176* | .023 | 8:1 |
| LA | 2168 | 1.490* | .060 | .191* | .013 | 8:1 |
| LA | 2184 | 1.220* | .070 | .144 | .014 | 8:1 |

TABLE 7-continued

Comparative Cherry weight and green bean weight per fruit for the 15 selected High Yielding Laurina Somaclones and Laurina controls from 1991 crop

| Genotype | Somaclone[a] Number | Cherry Weight (g) | STD | Green Weight (g) | STD | Ratio Cherry Weight/ Green Bean Wt. |
|---|---|---|---|---|---|---|
| LA | 2213 | 1.430* | .050 | .168* | .005 | 9:1 |
| LA | 2229 | 1.330 | .050 | .169* | .007 | 8:1 |
| LA | 2295 | 1.320 | .050 | .184* | .007 | 7:1 |
| LA | 2296 | 1.380 | .050 | .170* | .004 | 8:1 |
| LA | 2392 | 1.420* | .030 | .159 | .007 | 9:1 |
| LA | 2444 | 1.440* | .050 | .163* | .014 | 9:1 |
| LA | 2575 | 1.360 | .060 | .164* | .007 | 8:1 |
| LA | 2576 | 1.380 | .020 | .175* | .008 | 8:1 |
| LA | 2589 | 1.360 | .060 | .163* | .024 | 8:1 |
| LA | 3063 | 1.260 | .030 | .163* | .011 | 8:1 |
| Average | | 1.384* | .047 | .168* | .011 | 8:1 |
| Control | | 1.33 | .080 | .145 | .013 | 9:1 |

[a]Samples consisted of 100 fruits with four replicates per somaclone plant.

TABLE 8

Length of lateral branches of the 15 selected High Yielding Laurina Somaclones and Laurina controls evaluated in April 1991

| Genotype | Somaclone Number | Lateral Branch (cm)[a] Average | STD |
|---|---|---|---|
| LA | 2154 | 57.5* | 7.6 |
| LA | 2165 | 62.9* | 7.6 |
| LA | 2167 | 59.1* | 7.8 |
| LA | 2168 | ND | ND |
| LA | 2184 | 55.1* | 9.7 |
| LA | 2213 | 56.2* | 7.6 |
| LA | 2229 | 57.3* | 5.3 |
| LA | 2295 | 51.9* | 8.5 |
| LA | 2296 | 64.1* | 9.3 |
| LA | 2392 | 62.0* | 7.5 |
| LA | 2444 | 57.5* | 5.3 |
| LA | 2575 | 62.2* | 9.0 |
| LA | 2576 | 55.8* | 7.5 |
| LA | 2589 | 60.2* | 8.9 |
| LA | 3063 | 56.2* | 7.6 |
| Average | | 58.4* | 7.8 |
| Control | | 39.0 | 3.0 |

[a]Ten branches were evaluated per somaclone.

TABLE 9

Internode length of the 15 selected High Yielding Laurina Somaclones and Laurina controls evaluated in April 1991

| Genotype | Somaclone Number | Internode Length (cm)[a] Average | STD |
|---|---|---|---|
| LA | 2154 | 1.99* | .200 |
| LA | 2165 | 2.10* | .300 |
| LA | 2167 | 2.04* | .300 |
| LA | 2168 | ND | ND |
| LA | 2184 | 1.79 | .200 |
| LA | 2213 | 2.04* | .400 |
| LA | 2229 | 2.04* | .300 |
| LA | 2295 | 1.75 | .200 |
| LA | 2296 | 1.85* | .100 |
| LA | 2392 | 2.19* | .200 |
| LA | 2444 | 2.09* | .100 |
| LA | 2575 | 1.84* | .200 |
| LA | 2576 | 1.70 | .100 |
| LA | 2589 | 1.95* | .200 |
| LA | 3063 | 2.16* | .260 |
| Average | | 1.97* | .22 |
| Control | | 1.55 | .13 |

[a]Ten branches were evaluated per somaclone.

TABLE 10

Height, top and bottom width for the 15 selected High Yielding Laurina Somaclones and Laurina controls evaluated in April 1991

| Genotype | Somaclone Number | Height (m) | Width (m) Top | Width (m) Bottom |
|---|---|---|---|---|
| LA | 2154 | 2.10 | 1.10 | 1.60 |
| LA | 2165 | 1.76 | 1.30 | 1.45 |
| LA | 2167 | 1.91 | 0.94 | 1.60 |
| LA | 2168 | 1.82 | 1.10 | 1.43 |
| LA | 2184 | 1.68 | 1.05 | 1.42 |
| LA | 2213 | 2.00 | 1.10 | 1.50 |
| LA | 2229 | 1.90 | 1.15 | 1.45 |
| LA | 2295 | ND | ND | ND |
| LA | 2296 | 2.05 | .97 | 1.55 |
| LA | 2392 | 2.00 | 1.23 | 1.40 |
| LA | 2444 | 1.80 | 1.00 | 1.35 |
| LA | 2575 | 1.98 | 1.15 | 1.48 |
| LA | 2576 | 1.95 | 1.10 | 1.45 |
| LA | 2589 | 1.98 | 1.25 | 1.62 |
| LA | 3063 | 1.67 | 0.90 | 1.25 |
| Average | | 1.90* | 1.10* | 1.47* |
| STD | | 0.12 | 0.11 | 0.09 |
| Control | | 1.58 | 0.75 | 0.99 |
| STD | | 0.13 | 0.06 | 0.12 |

TABLE 11

Number of cherries per node for the 15 selected High Yielding Laurina Somaclones and Laurina controls evaluated in April 1991

| Genotype | Somaclone Number | Number of Cherries Per Node[a] Average | STD |
|---|---|---|---|
| LA | 2154 | 4.00 | 1.00 |
| LA | 2165 | 5.70 | 1.30* |
| LA | 2167 | 5.00 | 1.60* |
| LA | 2168 | ND | ND |
| LA | 2184 | 5.40 | 1.50* |
| LA | 2213 | 4.40 | 1.00 |
| LA | 2229 | 4.40 | 1.80* |
| LA | 2295 | 3.50 | 0.80 |
| LA | 2296 | 4.40 | 1.50* |
| LA | 2392 | 5.40 | 1.60* |
| LA | 2444 | 5.60 | 2.20* |
| LA | 2575 | 4.20 | 1.10 |
| LA | 2576 | 3.10 | 0.90 |
| LA | 2589 | 4.10 | 1.30 |
| LA | 3063 | 6.30 | 1.90* |
| Average | | 4.68* | 1.39 |
| Control | | 2.90 | 0.70 |

[a]Three nodes per branch and ten branches were evaluated per somaclone.

EXAMPLE 8

High-Yielding Laurina Somaclones: Caffeine Analysis

Caffeine analysis was made to verify the quality of caffeine in these high yielding mutants in accordance with the methods of Trugo et al. The recessive Laurina gene (lr lr) controls the reduction of caffeine level (50% from normal) and several morphological characteristics like small leaf area, short stature, short lateral branches, and elongated cherries and beans. Hence, caffeine determination made in 14 of the somaclones in this group established that these Laurina somaclones accumulated only 50% of the caffeine level found in normal Arabica varieties (Table 12), i.e., the average caffeine content of the selected somaclones was 0.62%.

TABLE 12

Caffeine values for the 15 selected High Yielding Laurina Somaclones and Laurina control from either 1989 or 1990 harvests

| Genotype | Somaclone Number | Caffeine % |
|---|---|---|
| LA | 2154 | .5800 |
| LA | 2165 | .5400 |
| LA | 2167 | .5800 |
| LA | 2168 | .6600 |
| LA | 2184 | .6700 |
| LA | 2213 | .6000 |
| LA | 2229 | .6400 |
| LA | 2295 | .6000 |
| LA | 2296 | .6000 |
| LA | 2392 | .6700 |
| LA | 2444 | ND |
| LA | 2575 | .5500 |
| LA | 2576 | .7000 |
| LA | 2589 | .6000 |
| LA | 3063 | .7100 |
| Average | | .6214 |
| STD | | .0518 |
| Control | | 0.659 |
| STD | | 0.110 |

EXAMPLE 9

High-Yielding Laurina Somaclones: Sugar and Oil Content Analysis

Free sugar determination revealed that two somaclones had less sucrose, six somaclones had more fructose, and three somaclones had more glucose relative to the controls. (Table 13). Sugar determinations were conducted in accordance with the methods described by Trugo et al.

The oil fraction in coffee is an excellent carrier of volatile components. Because Arabica coffee has more oil than Robusta, it may contribute to the superior Arabica beverage properties. The percentage of oil in the high-yielding Laurina somaclones was fully evaluated from coffee samples obtained from the 1991 and 1990 harvests for the majority of the selected Laurina somaclones (Table 14). The oil content analysis was based on an NMR method and was conducted in accordance with the methods of Hamilton et al (1986) *Analysis of Oils and Fats*, Elsevier Applied Science, London, and Theis et al. (1989) In: *Oil Crops of the World* (Robbelen t al; eds.) McGraw Hill, Toronto, pp. 132–164. No statistical differences in comparison with the control were observed for this parameter. Hence, the Laurina somaclones have maintained the desirable oil fraction associated with Arabica varieties.

TABLE 13

Sugar analysis of the 15 selected High Yielding Laurina somaclones and Laurina control for seeds harvested in 1991

| Genotype | Somaclone Number | Sucrose % | Fructose % | Glucose % |
|---|---|---|---|---|
| LA | 2154 | 10.220* | .530 | .350 |
| LA | 2165 | 10.620 | .600* | .430 |
| LA | 2167 | 10.610 | .440 | .340 |
| LA | 2168 | 10.800 | .540 | .390 |
| LA | 2184 | 10.860 | .379 | .270 |
| LA | 2213 | 10.340 | .870* | .630* |
| LA | 2229 | 10.090* | .540 | .380 |
| LA | 2295 | 10.730 | .430 | .320 |
| LA | 2296 | 10.980 | .590* | .410 |
| LA | 2392 | 11.400 | .530 | .400 |
| LA | 2444 | 10.460 | .770* | .520* |
| LA | 2575 | 10.640 | .500 | .400 |
| LA | 2576 | 10.900 | .730* | .560* |
| LA | 2589 | 11.260 | .600* | .430 |

TABLE 13-continued

Sugar analysis of the 15 selected High Yielding Laurina somaclones and Laurina control for seeds harvested in 1991

| Genotype | Somaclone Number | Sucrose % | Fructose % | Glucose % |
|---|---|---|---|---|
| LA | 3063 | 10.710 | .410 | .300 |
| Average | | 10.708 | .564* | .409 |
| STD | | .343 | .133 | .094 |
| Control | | 11.91 | 0.26 | 0.29 |

TABLE 14

Total oil content for the 15 selected High Yielding Laurina Somaclones and Laurina controls from 1991 and 1990 harvests

| Genotype | Somaclone Number | 1991 % | 1990 % |
|---|---|---|---|
| LA | 2154 | 15.300 | 11.840 |
| LA | 2165 | 15.160 | 14.450 |
| LA | 2167 | 15.760 | 14.710 |
| LA | 2168 | 15.570 | ND |
| LA | 2184 | 16.190 | 13.290 |
| LA | 2213 | 14.860 | 12.560 |
| LA | 2229 | 15.220 | ND |
| LA | 2295 | 15.360 | 12.600 |
| LA | 2296 | 14.640 | 13.430 |
| LA | 2392 | 14.810 | ND |
| LA | 2444 | 14.740 | ND |
| LA | 2575 | 15.000 | 11.960 |
| LA | 2576 | 14.000 | ND |
| LA | 2589 | 14.670 | 12.950 |
| LA | 3063 | 15.400 | 11.100 |
| Average | | 15.112 | 12.889 |
| STD | | .512 | 1.075 |
| Control | | 14.90 | 14.00 |
| STD | | 0.31 | 0.34 |

EXAMPLE 10

High-Yielding Laurina Somaclones: Other Chemical Constituents

Protein, trigonelin, chlorogenic acid, and total solids were evaluated for some of the 15 selected high yielding Laurina somaclones (Table 15). Data from 1990 crop showed that total protein ranged form 14.8%–16.2% in comparison to 15.8% for the Laurina controls. The values for trigonelin ranged from 1.2%–1.7% (control 1.5%), chlorogenic acid ranged from 6.3%–6.8% (control 6.7%), and total solids ranged from 30.5%–33.6% (control 32.6%). No statistical differences were found among the Laurina somaclones and the control plants for these parameters.

TABLE 15

Analytical data of the 15 selected High Yielding Laurina Somaclones and Laurina controls for 1990 harvest

| Genotype | Somaclone Number | Protein % | Trigonelin % | Chlorogenic Acid % | Total Solids % |
|---|---|---|---|---|---|
| LA | 2154 | 16.000 | 1.400 | 6.440 | 32.23 |
| LA | 2165 | 14.820 | 1.260 | 6.230 | 32.49 |
| LA | 2167 | 15.150 | 1.460 | 6.730 | 30.49 |
| LA | 2168 | 15.840 | 1.370 | 6.260 | 33.23 |
| LA | 2184 | ND | ND | ND | ND |
| LA | 2213 | 15.770 | 1.300 | 6.840 | 32.58 |
| LA | 2229 | ND | ND | ND | ND |
| LA | 2295 | 16.170 | 1.300 | 6.380 | 33.62 |
| LA | 2296 | 15.560 | 1.360 | 6.450 | 33.49 |
| LA | 2392 | ND | ND | ND | ND |
| LA | 2444 | ND | ND | ND | ND |
| LA | 2575 | 15.620 | 1.370 | 6.360 | 31.03 |
| LA | 2576 | ND | ND | ND | ND |

TABLE 15-continued

Analytical data of the 15 selected High Yielding Laurina Somaclones and Laurina controls for 1990 harvest

| Genotype | Somaclone Number | Protein % | Trigonelin % | Chlorogenic Acid % | Total Solids % |
|---|---|---|---|---|---|
| LA | 2589 | 16.200 | 1.680 | 6.820 | 32.45 |
| LA | 3063 | ND | ND | ND | ND |
| Average | | 15.681 | 1.389 | 6.501 | 32.40 |
| Controls | | 15.85 | 1.55 | 6.74 | 32.54 |

We claim:

1. A somaclonal variant of *Coffea arabica* cv. *Laurina* wherein said somaclonal variant exhibits green bean yield from about 115% to about 325% of average green bean yield of native Laurina plants and wherein said variant further exhibits caffeine content of about the average level of native Laurina plants.

2. A somaclonal variant of *Coffea arabica* cv. *Laurina* wherein said somaclonal variant exhibits cherry weight from about 118% to about 275% of average cherry weight of native Laurina plants and wherein said variant further exhibits caffeine content of about the average level of native Laurina plants.

3. The somaclonal variant according to claim 1 or 2 exhibiting levels of caffeine content from about 0.5% to about 0.7%.

4. A somaclonal variant of *Coffea arabica* cv. *Laurina* having ATCC accession number 75261.

5. A somaclonal variant of *Coffea arabica* cv. *Laurina* having ATCC accession number 75262.

* * * * *